(12) United States Patent
Abdeen et al.

(10) Patent No.: US 11,848,090 B2
(45) Date of Patent: Dec. 19, 2023

(54) TRAINER FOR A NEUROSTIMULATOR PROGRAMMER AND ASSOCIATED METHODS OF USE WITH A NEUROSTIMULATION SYSTEM

(71) Applicant: Axonics, Inc., Irvine, CA (US)

(72) Inventors: Faizal Abdeen, Mission Viejo, CA (US); Charles Borlase, Lake Forest, CA (US); Prabodh Mathur, Laguna Niguel, CA (US); Rabih Nassif, Santa Ana, CA (US); Flavio Ono, Aliso Viejo, CA (US); Franklin S. Portillo, Norco, CA (US); John Woock, Costa Mesa, CA (US)

(73) Assignee: AXONICS, INC., Irvine, CA (US)

( * ) Notice: Subject to any disclaimer, the term of this patent is extended or adjusted under 35 U.S.C. 154(b) by 882 days.

(21) Appl. No.: 16/880,918

(22) Filed: May 21, 2020

(65) Prior Publication Data

US 2020/0372996 A1 Nov. 26, 2020

Related U.S. Application Data

(60) Provisional application No. 62/852,875, filed on May 24, 2019.

(51) Int. Cl.
*A61B 5/00* (2006.01)
*A61B 5/0205* (2006.01)
(Continued)

(52) U.S. Cl.
CPC ......... *G16H 20/30* (2018.01); *A61N 1/36007* (2013.01); *A61N 1/372* (2013.01);
(Continued)

(58) Field of Classification Search
CPC .... G16H 20/30; G16H 50/50; A61N 1/36007; A61N 1/372; A61N 1/37264; G01R 27/02; G09B 19/0053; G09B 23/28
See application file for complete search history.

(56) References Cited

U.S. PATENT DOCUMENTS

| 53,928 A | 4/1866 | Sheffield et al. |
| 3,057,356 A | 10/1962 | Greatbatch |
| (Continued) | | |

FOREIGN PATENT DOCUMENTS

| AT | 520440 | 9/2011 |
| AU | 4664800 | 11/2000 |
| (Continued) | | |

OTHER PUBLICATIONS

US 9,601,939 B2, 03/2017, Cong et al. (withdrawn)
(Continued)

*Primary Examiner* — Thuy Dao
(74) *Attorney, Agent, or Firm* — Gordon Rees Scully Mansukhani, LLP

(57) ABSTRACT

A training system for a neurostimulation system that may be used to simulate a neurostimulator programming session and/or lead placement. The system may include a training device that may be coupled to a neurostimulator programmer and may include an interface to allow user interaction and/or display information relevant to the stimulation. The trainer device may include circuitry for simulating a neurostimulator such as an IPG or EPG, and may include circuitry for simulating impedance associated with lead placement.

27 Claims, 12 Drawing Sheets

(51) Int. Cl.

| | | |
|---|---|---|
| G06F 9/445 | (2018.01) | |
| G06F 9/455 | (2018.01) | |
| G16H 20/30 | (2018.01) | |
| A61N 1/372 | (2006.01) | |
| A61N 1/36 | (2006.01) | |
| G09B 19/00 | (2006.01) | |
| G01R 27/02 | (2006.01) | |
| G16H 50/50 | (2018.01) | |
| G09B 23/28 | (2006.01) | |

(52) U.S. Cl.
CPC ......... *A61N 1/37264* (2013.01); *G01R 27/02* (2013.01); *G09B 19/0053* (2013.01); *G09B 23/28* (2013.01); *G16H 50/50* (2018.01)

(56) References Cited

U.S. PATENT DOCUMENTS

| | | |
|---|---|---|
| 3,348,548 A | 10/1967 | Chardack |
| 3,646,940 A | 3/1972 | Timm et al. |
| 3,824,129 A | 7/1974 | Fagan, Jr. |
| 3,825,015 A | 7/1974 | Berkovits |
| 3,888,260 A | 6/1975 | Fischell |
| 3,902,501 A | 9/1975 | Citron et al. |
| 3,939,843 A | 2/1976 | Smyth |
| 3,942,535 A | 3/1976 | Schulman |
| 3,970,912 A | 7/1976 | Hoffman |
| 3,995,623 A | 12/1976 | Blake et al. |
| 4,019,518 A | 4/1977 | Maurer et al. |
| 4,044,774 A | 8/1977 | Corbin et al. |
| 4,082,097 A | 4/1978 | Mann et al. |
| 4,141,365 A | 2/1979 | Fischell et al. |
| 4,166,469 A | 9/1979 | Littleford |
| 4,210,383 A | 7/1980 | Davis |
| 4,269,198 A | 5/1981 | Stokes |
| 4,285,347 A | 8/1981 | Hess |
| 4,340,062 A | 7/1982 | Thompson et al. |
| 4,379,462 A | 4/1983 | Borkan et al. |
| 4,407,303 A | 10/1983 | Akerstrom |
| 4,437,475 A | 3/1984 | White |
| 4,468,723 A | 8/1984 | Hughes |
| 4,512,351 A | 4/1985 | Pohndorf |
| 4,550,731 A | 11/1985 | Batina et al. |
| 4,558,702 A | 12/1985 | Barreras et al. |
| 4,654,880 A | 3/1987 | Sontag |
| 4,662,382 A | 5/1987 | Sluetz et al. |
| 4,673,867 A | 6/1987 | Davis |
| 4,719,919 A | 1/1988 | Marchosky et al. |
| 4,721,118 A | 1/1988 | Harris |
| 4,722,353 A | 2/1988 | Sluetz |
| 4,744,371 A | 5/1988 | Harris |
| 4,800,898 A | 1/1989 | Hess et al. |
| 4,848,352 A | 7/1989 | Pohndorf et al. |
| 4,860,446 A | 8/1989 | Lessar et al. |
| 4,957,118 A | 9/1990 | Erlebacher |
| 4,989,617 A | 2/1991 | Memberg et al. |
| 5,012,176 A | 4/1991 | Laforge |
| 5,052,407 A | 10/1991 | Hauser et al. |
| 5,143,089 A | 9/1992 | Alt |
| 5,193,539 A | 3/1993 | Schulman et al. |
| 5,197,466 A | 3/1993 | Marchosky et al. |
| 5,204,611 A | 4/1993 | Nor et al. |
| 5,255,691 A | 10/1993 | Otten |
| 5,257,634 A | 11/1993 | Kroll |
| 5,342,408 A | 8/1994 | deCoriolis et al. |
| 5,439,485 A | 8/1995 | Mar et al. |
| 5,476,499 A | 12/1995 | Hirschberg |
| 5,484,445 A | 1/1996 | Knuth |
| 5,571,148 A | 11/1996 | Loeb et al. |
| 5,592,070 A | 1/1997 | Mino |
| 5,637,981 A | 6/1997 | Nagai et al. |
| 5,676,162 A | 10/1997 | Larson, Jr. et al. |
| 5,690,693 A | 11/1997 | Wang et al. |
| 5,702,428 A | 12/1997 | Tippey et al. |
| 5,702,431 A | 12/1997 | Wang et al. |
| 5,712,795 A | 1/1998 | Layman et al. |
| 5,713,939 A | 2/1998 | Nedungadi et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,871,532 A | 2/1999 | Schroeppel |
| 5,876,423 A | 3/1999 | Braun |
| 5,877,472 A | 3/1999 | Campbell et al. |
| 5,902,331 A | 5/1999 | Bonner et al. |
| 5,948,006 A | 9/1999 | Mann |
| 5,949,632 A | 9/1999 | Barreras, Sr. et al. |
| 5,957,965 A | 9/1999 | Moumane et al. |
| 5,974,344 A | 10/1999 | Shoemaker, II et al. |
| 5,991,665 A | 11/1999 | Wang et al. |
| 6,014,588 A | 1/2000 | Fitz |
| 6,027,456 A | 2/2000 | Feler et al. |
| 6,035,237 A | 3/2000 | Schulman et al. |
| 6,052,624 A | 4/2000 | Mann |
| 6,055,456 A | 4/2000 | Gerber |
| 6,057,513 A | 5/2000 | Ushikoshi et al. |
| 6,067,474 A | 5/2000 | Schulman et al. |
| 6,075,339 A | 6/2000 | Reipur et al. |
| 6,076,017 A | 6/2000 | Taylor et al. |
| 6,081,097 A | 6/2000 | Seri et al. |
| 6,083,247 A | 7/2000 | Rutten et al. |
| 6,104,957 A | 8/2000 | Alo et al. |
| 6,104,960 A | 8/2000 | Duysens et al. |
| 6,138,681 A | 10/2000 | Chen et al. |
| 6,157,861 A | 12/2000 | Faltys et al. |
| 6,164,284 A | 12/2000 | Schulman et al. |
| 6,165,180 A | 12/2000 | Cigaina et al. |
| 6,166,518 A | 12/2000 | Echarri et al. |
| 6,169,387 B1 | 1/2001 | Kaib |
| 6,172,556 B1 | 1/2001 | Prentice |
| 6,178,353 B1 | 1/2001 | Griffith et al. |
| 6,181,105 B1 | 1/2001 | Cutolo et al. |
| 6,181,961 B1 | 1/2001 | Prass |
| 6,185,452 B1 | 2/2001 | Schulman et al. |
| 6,191,365 B1 | 2/2001 | Avellanet |
| 6,208,894 B1 | 3/2001 | Schulman et al. |
| 6,208,895 B1 | 3/2001 | Sullivan et al. |
| 6,212,430 B1 | 4/2001 | Kung |
| 6,212,431 B1 | 4/2001 | Hahn et al. |
| 6,221,513 B1 | 4/2001 | Lasater |
| 6,227,204 B1 | 5/2001 | Baumann et al. |
| 6,243,608 B1 | 6/2001 | Pauly et al. |
| 6,246,911 B1 | 6/2001 | Seligman |
| 6,249,703 B1 | 6/2001 | Stanton et al. |
| 6,265,789 B1 | 7/2001 | Honda et al. |
| 6,275,737 B1 | 8/2001 | Mann |
| 6,278,258 B1 | 8/2001 | Echarri et al. |
| 6,305,381 B1 | 10/2001 | Weijand et al. |
| 6,306,100 B1 | 10/2001 | Prass |
| 6,313,779 B1 | 11/2001 | Leung et al. |
| 6,314,325 B1 | 11/2001 | Fitz |
| 6,315,721 B2 | 11/2001 | Schulman et al. |
| 6,316,909 B1 | 11/2001 | Honda et al. |
| 6,321,118 B1 | 11/2001 | Hahn |
| 6,324,432 B1 | 11/2001 | Rigaux et al. |
| 6,327,504 B1 | 12/2001 | Dolgin et al. |
| 6,354,991 B1 | 3/2002 | Gross et al. |
| 6,360,750 B1 | 3/2002 | Gerber et al. |
| 6,381,496 B1 | 4/2002 | Meadows et al. |
| 6,393,325 B1 | 5/2002 | Mann et al. |
| 6,427,086 B1 | 7/2002 | Fischell et al. |
| 6,438,423 B1 | 8/2002 | Rezai et al. |
| 6,442,434 B1 | 8/2002 | Zarinetchi et al. |
| 6,453,198 B1 | 9/2002 | Torgerson et al. |
| 6,466,817 B1 | 10/2002 | Kaula et al. |
| 6,473,652 B1 | 10/2002 | Sarwal et al. |
| 6,500,141 B1 | 12/2002 | Irion et al. |
| 6,505,075 B1 | 1/2003 | Weiner |
| 6,505,077 B1 | 1/2003 | Kast et al. |
| 6,510,347 B2 | 1/2003 | Borkan |
| 6,516,227 B1 | 2/2003 | Meadows et al. |
| 6,517,227 B2 | 2/2003 | Stidham et al. |
| 6,521,350 B2 | 2/2003 | Fey et al. |
| 6,542,846 B1 | 4/2003 | Miller et al. |
| 6,553,263 B1 | 4/2003 | Meadows et al. |

(56) References Cited

U.S. PATENT DOCUMENTS

| | | |
|---|---|---|
| 6,564,807 B1 | 5/2003 | Schulman et al. |
| 6,584,355 B2 | 6/2003 | Stessman |
| 6,587,728 B2 | 7/2003 | Fang et al. |
| 6,600,954 B2 | 7/2003 | Cohen et al. |
| 6,609,031 B1 | 8/2003 | Law et al. |
| 6,609,032 B1 | 8/2003 | Woods et al. |
| 6,609,945 B2 | 8/2003 | Jimenez et al. |
| 6,625,494 B2 | 9/2003 | Fang et al. |
| 6,652,449 B1 | 11/2003 | Gross et al. |
| 6,654,634 B1 | 11/2003 | Prass |
| 6,662,051 B1 | 12/2003 | Eraker et al. |
| 6,662,053 B2 | 12/2003 | Borkan |
| 6,664,763 B2 | 12/2003 | Echarri et al. |
| 6,678,563 B2 | 1/2004 | Fang et al. |
| 6,685,638 B1 | 2/2004 | Taylor et al. |
| 6,701,189 B2 | 3/2004 | Fang et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,836,685 B1 | 12/2004 | Fitz |
| 6,847,849 B2 | 1/2005 | Mamo et al. |
| 6,864,755 B2 | 3/2005 | Moore |
| 6,871,099 B1 | 3/2005 | Whitehurst et al. |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,907,293 B2 | 6/2005 | Grill et al. |
| 6,923,814 B1 | 8/2005 | Hildebrand et al. |
| 6,941,171 B2 | 9/2005 | Mann et al. |
| 6,959,215 B2 | 10/2005 | Gliner et al. |
| 6,971,393 B1 | 12/2005 | Mamo et al. |
| 6,986,453 B2 | 1/2006 | Jiang et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,010,351 B2 | 3/2006 | Firlik et al. |
| 7,024,247 B2 | 4/2006 | Gliner et al. |
| 7,043,304 B1 | 5/2006 | Griffith et al. |
| 7,047,078 B2 | 5/2006 | Boggs, II et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,114,502 B2 | 10/2006 | Schulman et al. |
| 7,127,298 B1 | 10/2006 | He et al. |
| 7,131,996 B2 | 11/2006 | Wasserman et al. |
| 7,142,925 B1 | 11/2006 | Bhadra et al. |
| 7,146,217 B2 | 12/2006 | Firlik et al. |
| 7,146,219 B2 | 12/2006 | Sieracki et al. |
| 7,151,914 B2 | 12/2006 | Brewer |
| 7,167,743 B2 | 1/2007 | Heruth et al. |
| 7,167,749 B2 | 1/2007 | Biggs et al. |
| 7,167,756 B1 | 1/2007 | Torgerson et al. |
| 7,177,677 B2 | 2/2007 | Kaula et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,184,836 B1 | 2/2007 | Meadows et al. |
| 7,187,978 B2 | 3/2007 | Malek et al. |
| 7,191,005 B2 | 3/2007 | Stessman |
| 7,212,110 B1 | 5/2007 | Martin et al. |
| 7,214,197 B2 | 5/2007 | Prass |
| 7,216,001 B2 | 5/2007 | Hacker et al. |
| 7,225,028 B2 | 5/2007 | Della Santina et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,236,831 B2 | 6/2007 | Firlik et al. |
| 7,239,918 B2 | 7/2007 | Strother et al. |
| 7,245,972 B2 | 7/2007 | Davis |
| 7,283,867 B2 | 10/2007 | Strother et al. |
| 7,286,880 B2 | 10/2007 | Olson et al. |
| 7,295,878 B1 | 11/2007 | Meadows et al. |
| 7,299,096 B2 | 11/2007 | Balzer et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,326,181 B2 | 2/2008 | Katims |
| 7,328,068 B2 | 2/2008 | Spinelli et al. |
| 7,330,764 B2 | 2/2008 | Swoyer et al. |
| 7,331,499 B2 | 2/2008 | Jiang et al. |
| 7,337,006 B2 | 2/2008 | Kim et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,395,113 B2 | 7/2008 | Heruth et al. |
| 7,396,265 B2 | 7/2008 | Darley et al. |
| 7,406,351 B2 | 7/2008 | Wesselink |
| 7,415,308 B2 | 8/2008 | Gerber et al. |
| 7,444,181 B2 | 10/2008 | Shi et al. |
| 7,444,184 B2 | 10/2008 | Boveja et al. |
| 7,447,546 B2 | 11/2008 | Kim et al. |
| 7,450,991 B2 | 11/2008 | Smith et al. |
| 7,450,993 B2 | 11/2008 | Kim et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,747 B2 | 1/2009 | Gliner et al. |
| 7,483,752 B2 | 1/2009 | Von Arx et al. |
| 7,486,048 B2 | 2/2009 | Tsukamoto et al. |
| 7,496,404 B2 | 2/2009 | Meadows et al. |
| 7,502,651 B2 | 3/2009 | Kim et al. |
| 7,513,257 B2 | 4/2009 | Schulman et al. |
| 7,515,965 B2 | 4/2009 | Gerber et al. |
| 7,515,967 B2 | 4/2009 | Phillips et al. |
| 7,522,953 B2 | 4/2009 | Kaula et al. |
| 7,532,936 B2 | 5/2009 | Erickson et al. |
| 7,539,538 B2 | 5/2009 | Parramon et al. |
| 7,551,958 B2 | 6/2009 | Libbus et al. |
| 7,551,960 B2 | 6/2009 | Forsberg et al. |
| 7,555,346 B1 | 6/2009 | Woods et al. |
| 7,555,347 B2 | 6/2009 | Loeb |
| 7,565,199 B2 | 7/2009 | Sheffield et al. |
| 7,565,203 B2 | 7/2009 | Greenberg et al. |
| 7,571,000 B2 | 8/2009 | Boggs, II et al. |
| 7,577,481 B2 | 8/2009 | Firlik et al. |
| 7,578,819 B2 | 8/2009 | Bleich et al. |
| 7,580,752 B2 | 8/2009 | Gerber et al. |
| 7,580,753 B2 | 8/2009 | Kim et al. |
| 7,582,053 B2 | 9/2009 | Gross et al. |
| 7,582,058 B1 | 9/2009 | Miles et al. |
| 7,613,516 B2 | 11/2009 | Cohen et al. |
| 7,617,002 B2 | 11/2009 | Goetz |
| 7,620,456 B2 | 11/2009 | Gliner et al. |
| 7,623,925 B2 | 11/2009 | Grill et al. |
| 7,636,602 B2 | 12/2009 | Baru Fassio et al. |
| 7,640,059 B2 | 12/2009 | Forsberg et al. |
| 7,643,880 B2 | 1/2010 | Tanagho et al. |
| 7,647,117 B2 | 1/2010 | Bauhahn |
| 7,650,192 B2 | 1/2010 | Wahlstrand |
| 7,664,544 B2 | 2/2010 | Miles et al. |
| 7,672,730 B2 | 3/2010 | Firlik et al. |
| 7,706,889 B2 | 4/2010 | Gerber et al. |
| 7,720,547 B2 | 5/2010 | Denker et al. |
| 7,720,548 B2 | 5/2010 | King |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,756,584 B2 | 7/2010 | Sheffield et al. |
| 7,771,838 B1 | 8/2010 | He et al. |
| 7,774,069 B2 | 8/2010 | Olson et al. |
| 7,801,601 B2 | 9/2010 | Maschino et al. |
| 7,801,619 B2 | 9/2010 | Gerber et al. |
| 7,805,196 B2 | 9/2010 | Miesel et al. |
| 7,813,803 B2 | 10/2010 | Heruth et al. |
| 7,813,809 B2 | 10/2010 | Strother et al. |
| 7,819,909 B2 | 10/2010 | Goetz et al. |
| 7,826,901 B2 | 11/2010 | Lee et al. |

(56) References Cited

U.S. PATENT DOCUMENTS

| | | |
|---|---|---|
| 7,831,305 B2 | 11/2010 | Gliner |
| 7,848,818 B2 | 12/2010 | Barolat et al. |
| 7,853,322 B2 | 12/2010 | Bourget et al. |
| 7,878,207 B2 | 2/2011 | Goetz et al. |
| 7,890,176 B2 | 2/2011 | Jaax et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,945,330 B2 | 5/2011 | Gliner et al. |
| 7,952,349 B2 | 5/2011 | Huang et al. |
| 7,957,797 B2 | 6/2011 | Bourget et al. |
| 7,957,809 B2 | 6/2011 | Bourget et al. |
| 7,957,818 B2 | 6/2011 | Swoyer |
| 7,962,218 B2 | 6/2011 | Balzer et al. |
| 7,966,073 B2 | 6/2011 | Pless et al. |
| 7,979,119 B2 | 7/2011 | Kothandaraman et al. |
| 7,979,126 B2 | 7/2011 | Payne et al. |
| 7,981,144 B2 | 7/2011 | Geist et al. |
| 7,988,507 B2 | 8/2011 | Darley et al. |
| 8,000,782 B2 | 8/2011 | Gharib et al. |
| 8,000,800 B2 | 8/2011 | Takeda et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,019,425 B2 | 9/2011 | Firlik et al. |
| 8,024,047 B2 | 9/2011 | Olson et al. |
| 8,027,716 B2 | 9/2011 | Gharib et al. |
| 8,036,756 B2 | 10/2011 | Swoyer et al. |
| 8,044,635 B2 | 10/2011 | Peterson |
| 8,050,753 B2 | 11/2011 | Libbus et al. |
| 8,050,767 B2 | 11/2011 | Sheffield et al. |
| 8,050,768 B2 | 11/2011 | Firlik et al. |
| 8,050,769 B2 | 11/2011 | Gharib et al. |
| 8,055,337 B2 | 11/2011 | Moffitt et al. |
| 8,055,349 B2 | 11/2011 | Gharib et al. |
| 8,065,012 B2 | 11/2011 | Firlik et al. |
| 8,068,912 B2 | 11/2011 | Kaula et al. |
| 8,073,546 B2 | 12/2011 | Sheffield et al. |
| 8,082,039 B2 | 12/2011 | Kim et al. |
| 8,083,663 B2 | 12/2011 | Gross et al. |
| 8,103,360 B2 | 1/2012 | Foster |
| 8,108,049 B2 | 1/2012 | King |
| 8,112,155 B2 | 2/2012 | Einav et al. |
| 8,116,862 B2 | 2/2012 | Stevenson et al. |
| 8,121,701 B2 | 2/2012 | Woods et al. |
| 8,121,702 B2 | 2/2012 | King |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,147,421 B2 | 4/2012 | Farquhar et al. |
| 8,150,530 B2 | 4/2012 | Wesselink |
| 8,155,753 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,182,423 B2 | 5/2012 | Miles et al. |
| 8,190,262 B2 | 5/2012 | Gerber et al. |
| 8,195,300 B2 | 6/2012 | Gliner et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,224,452 B2 | 7/2012 | Pless et al. |
| 8,224,460 B2 | 7/2012 | Schleicher et al. |
| 8,229,565 B2 | 7/2012 | Kim et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,326,433 B2 | 12/2012 | Blum et al. |
| 8,332,040 B1 | 12/2012 | Winstrom |
| 8,337,410 B2 | 12/2012 | Kelleher et al. |
| 8,340,786 B2 | 12/2012 | Gross et al. |
| 8,362,742 B2 | 1/2013 | Kallmyer |
| 8,369,943 B2 | 2/2013 | Shuros et al. |
| 8,380,314 B2 | 2/2013 | Panken et al. |
| 8,382,059 B2 | 2/2013 | Le Gette et al. |
| 8,386,048 B2 | 2/2013 | McClure et al. |
| 8,391,972 B2 | 3/2013 | Libbus et al. |
| 8,396,555 B2 | 3/2013 | Boggs, II et al. |
| 8,412,335 B2 | 4/2013 | Gliner et al. |
| 8,417,346 B2 | 4/2013 | Giftakis et al. |
| 8,423,145 B2 | 4/2013 | Pless et al. |
| 8,423,146 B2 | 4/2013 | Giftakis et al. |
| 8,430,805 B2 | 4/2013 | Burnett et al. |
| 8,433,414 B2 | 4/2013 | Gliner et al. |
| 8,435,166 B2 | 5/2013 | Burnett et al. |
| 8,447,402 B1 | 5/2013 | Jiang et al. |
| 8,447,408 B2 | 5/2013 | North et al. |
| 8,452,409 B2 | 5/2013 | Bachinski et al. |
| 8,457,756 B2 | 6/2013 | Rahman |
| 8,457,758 B2 | 6/2013 | Olson et al. |
| 8,467,875 B2 | 6/2013 | Bennett et al. |
| 8,480,437 B2 | 7/2013 | Dilmaghanian et al. |
| 8,483,839 B2 | 7/2013 | Wesselink |
| 8,494,625 B2 | 7/2013 | Hargrove |
| 8,509,919 B2 | 8/2013 | Yoo et al. |
| 8,515,545 B2 | 8/2013 | Trier |
| 8,538,530 B1 | 9/2013 | Orinski |
| 8,543,223 B2 | 9/2013 | Sage et al. |
| 8,544,322 B2 | 10/2013 | Minami et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,588,927 B2 | 11/2013 | Roy et al. |
| 8,612,002 B2 | 12/2013 | Faltys et al. |
| 8,620,436 B2 | 12/2013 | Parramon et al. |
| 8,626,314 B2 | 1/2014 | Swoyer et al. |
| 8,634,904 B2 | 1/2014 | Kaula et al. |
| 8,634,932 B1 | 1/2014 | Ye et al. |
| 8,644,931 B2 | 2/2014 | Stadler et al. |
| 8,644,933 B2 | 2/2014 | Ozawa et al. |
| 8,644,940 B2 | 2/2014 | Forsell |
| 8,655,451 B2 | 2/2014 | Klosterman et al. |
| 8,655,455 B2 | 2/2014 | Mann et al. |
| 8,672,840 B2 | 3/2014 | Miles et al. |
| 8,694,115 B2 | 4/2014 | Goetz et al. |
| 8,700,175 B2 | 4/2014 | Fell |
| 8,700,177 B2 | 4/2014 | Strother et al. |
| 8,706,239 B2 | 4/2014 | Bharmi et al. |
| 8,706,254 B2 | 4/2014 | Vamos et al. |
| 8,712,546 B2 | 4/2014 | Kim et al. |
| 8,725,262 B2 | 5/2014 | Olson et al. |
| 8,725,269 B2 | 5/2014 | Nolan et al. |
| 8,731,656 B2 | 5/2014 | Bourget et al. |
| 8,738,138 B2 | 5/2014 | Funderburk et al. |
| 8,738,141 B2 | 5/2014 | Smith et al. |
| 8,738,148 B2 | 5/2014 | Olson et al. |
| 8,740,783 B2 | 6/2014 | Gharib et al. |
| 8,744,585 B2 | 6/2014 | Gerber et al. |
| 8,750,985 B2 | 6/2014 | Parramon et al. |
| 8,751,008 B2 | 6/2014 | Carlton et al. |
| 8,761,897 B2 | 6/2014 | Kaula et al. |
| 8,768,450 B2 | 7/2014 | Gharib et al. |
| 8,768,452 B2 | 7/2014 | Gerber |
| 8,774,912 B2 | 7/2014 | Gerber |
| 8,805,518 B2 | 8/2014 | King et al. |
| 8,812,116 B2 | 8/2014 | Kaula et al. |
| 8,825,163 B2 | 9/2014 | Grill et al. |
| 8,825,175 B2 | 9/2014 | King |
| 8,831,731 B2 | 9/2014 | Blum et al. |

(56) References Cited

U.S. PATENT DOCUMENTS

| | | |
|---|---|---|
| 8,831,737 B2 | 9/2014 | Wesselink |
| 8,849,632 B2 | 9/2014 | Sparks et al. |
| 8,855,767 B2 | 10/2014 | Faltys et al. |
| 8,855,773 B2 | 10/2014 | Kokones et al. |
| 8,868,199 B2 | 10/2014 | Kaula et al. |
| 8,892,217 B2 | 11/2014 | Camps et al. |
| 8,903,486 B2 | 12/2014 | Bourget et al. |
| 8,918,174 B2 | 12/2014 | Woods et al. |
| 8,918,184 B1 | 12/2014 | Torgerson et al. |
| 8,954,148 B2 | 2/2015 | Labbe et al. |
| 8,989,861 B2 | 3/2015 | Su et al. |
| 9,031,658 B2 | 5/2015 | Chiao et al. |
| 9,044,592 B2 | 6/2015 | Imran et al. |
| 9,050,473 B2 | 6/2015 | Woods et al. |
| 9,089,712 B2 | 7/2015 | Joshi et al. |
| 9,108,063 B2 | 8/2015 | Olson et al. |
| 9,144,680 B2 | 9/2015 | Kaula et al. |
| 9,149,635 B2 | 10/2015 | Denison et al. |
| 9,155,885 B2 | 10/2015 | Wei et al. |
| 9,166,321 B2 | 10/2015 | Smith et al. |
| 9,168,374 B2 | 10/2015 | Su |
| 9,192,763 B2 | 11/2015 | Gerber et al. |
| 9,197,173 B2 | 11/2015 | Denison et al. |
| 9,199,075 B1 | 12/2015 | Westlund |
| 9,205,255 B2 | 12/2015 | Strother et al. |
| 9,209,634 B2 | 12/2015 | Cottrill et al. |
| 9,216,294 B2 | 12/2015 | Bennett et al. |
| 9,227,055 B2 | 1/2016 | Wahlstrand et al. |
| 9,227,076 B2 | 1/2016 | Sharma et al. |
| 9,238,135 B2 | 1/2016 | Goetz et al. |
| 9,240,630 B2 | 1/2016 | Joshi |
| 9,242,090 B2 | 1/2016 | Atalar et al. |
| 9,244,898 B2 | 1/2016 | Vamos et al. |
| 9,248,292 B2 | 2/2016 | Trier et al. |
| 9,259,578 B2 | 2/2016 | Torgerson |
| 9,259,582 B2 | 2/2016 | Joshi et al. |
| 9,265,958 B2 | 2/2016 | Joshi et al. |
| 9,270,134 B2 | 2/2016 | Gaddam et al. |
| 9,272,140 B2 | 3/2016 | Gerber |
| 9,283,394 B2 | 3/2016 | Whitehurst et al. |
| 9,295,851 B2 | 3/2016 | Gordon et al. |
| 9,308,022 B2 | 4/2016 | Chitre et al. |
| 9,308,382 B2 | 4/2016 | Strother et al. |
| 9,314,616 B2 | 4/2016 | Wells et al. |
| 9,320,899 B2 | 4/2016 | Parramon et al. |
| 9,333,339 B2 | 5/2016 | Weiner |
| 9,352,148 B2 | 5/2016 | Stevenson et al. |
| 9,352,150 B2 | 5/2016 | Stevenson et al. |
| 9,358,039 B2 | 6/2016 | Kimmel et al. |
| 9,364,658 B2 | 6/2016 | Wechter |
| 9,375,574 B2 | 6/2016 | Kaula et al. |
| 9,393,423 B2 | 7/2016 | Parramon et al. |
| 9,399,137 B2 | 7/2016 | Parker et al. |
| 9,409,020 B2 | 8/2016 | Parker |
| 9,415,211 B2 | 8/2016 | Bradley et al. |
| 9,427,571 B2 | 8/2016 | Sage et al. |
| 9,427,573 B2 | 8/2016 | Gindele et al. |
| 9,427,574 B2 | 8/2016 | Lee et al. |
| 9,433,783 B2 | 9/2016 | Wei et al. |
| 9,436,481 B2 | 9/2016 | Drew |
| 9,446,245 B2 | 9/2016 | Grill et al. |
| 9,463,324 B2 | 10/2016 | Olson et al. |
| 9,468,755 B2 | 10/2016 | Westlund et al. |
| 9,471,753 B2 | 10/2016 | Kaula et al. |
| 9,480,846 B2 | 11/2016 | Strother et al. |
| 9,492,672 B2 | 11/2016 | Vamos et al. |
| 9,492,675 B2 | 11/2016 | Torgerson et al. |
| 9,492,678 B2 | 11/2016 | Chow |
| 9,498,628 B2 | 11/2016 | Kaemmerer et al. |
| 9,502,754 B2 | 11/2016 | Zhao et al. |
| 9,504,830 B2 | 11/2016 | Kaula et al. |
| 9,522,282 B2 | 12/2016 | Chow et al. |
| 9,533,155 B2 | 1/2017 | Jiang et al. |
| 9,555,246 B2 | 1/2017 | Jiang et al. |
| 9,561,372 B2 | 2/2017 | Jiang et al. |
| 9,592,389 B2 | 3/2017 | Moffitt |
| 9,610,449 B2 | 4/2017 | Kaula et al. |
| 9,615,744 B2 | 4/2017 | Denison et al. |
| 9,623,257 B2 | 4/2017 | Olson et al. |
| 9,636,497 B2 | 5/2017 | Bradley et al. |
| 9,643,004 B2 | 5/2017 | Gerber |
| 9,653,935 B2 | 5/2017 | Cong et al. |
| 9,656,074 B2 | 5/2017 | Simon et al. |
| 9,656,076 B2 | 5/2017 | Trier et al. |
| 9,656,089 B2 | 5/2017 | Yip et al. |
| 9,675,809 B2 | 6/2017 | Chow |
| 9,687,649 B2 | 6/2017 | Thacker |
| 9,707,405 B2 | 7/2017 | Shishilla et al. |
| 9,713,706 B2 | 7/2017 | Gerber |
| 9,717,900 B2 | 8/2017 | Swoyer et al. |
| 9,724,526 B2 | 8/2017 | Strother et al. |
| 9,731,116 B2 | 8/2017 | Chen |
| 9,737,704 B2 | 8/2017 | Wahlstrand et al. |
| 9,744,347 B2 | 8/2017 | Chen et al. |
| 9,750,930 B2 | 9/2017 | Chen |
| 9,757,555 B2 | 9/2017 | Novotny et al. |
| 9,764,147 B2 | 9/2017 | Torgerson |
| 9,767,255 B2 | 9/2017 | Kaula et al. |
| 9,776,002 B2 | 10/2017 | Parker et al. |
| 9,776,006 B2 | 10/2017 | Parker et al. |
| 9,776,007 B2 | 10/2017 | Kaula et al. |
| 9,782,596 B2 | 10/2017 | Vamos et al. |
| 9,802,051 B2 | 10/2017 | Mathur et al. |
| 9,814,884 B2 | 11/2017 | Parker et al. |
| 9,821,112 B2 | 11/2017 | Olson et al. |
| 9,827,415 B2 | 11/2017 | Stevenson et al. |
| 9,827,424 B2 | 11/2017 | Kaula et al. |
| 9,833,614 B1 | 12/2017 | Gliner |
| 9,849,278 B2 | 12/2017 | Spinelli et al. |
| 9,855,423 B2 | 1/2018 | Jiang et al. |
| 9,855,438 B2 | 1/2018 | Parramon et al. |
| 9,872,988 B2 | 1/2018 | Kaula et al. |
| 9,878,165 B2 | 1/2018 | Wilder et al. |
| 9,878,168 B2 | 1/2018 | Shishilla et al. |
| 9,882,420 B2 | 1/2018 | Cong et al. |
| 9,884,198 B2 | 2/2018 | Parker |
| 9,889,292 B2 | 2/2018 | Gindele et al. |
| 9,889,293 B2 | 2/2018 | Siegel et al. |
| 9,889,306 B2 | 2/2018 | Stevenson et al. |
| 9,895,532 B2 | 2/2018 | Kaula et al. |
| 9,895,546 B2 | 2/2018 | Jiang et al. |
| 9,899,778 B2 | 2/2018 | Hanson et al. |
| 9,901,284 B2 | 2/2018 | Olsen et al. |
| 9,901,740 B2 | 2/2018 | Drees et al. |
| 9,907,476 B2 | 3/2018 | Bonde et al. |
| 9,907,955 B2 | 3/2018 | Bakker et al. |
| 9,907,957 B2 | 3/2018 | Woods et al. |
| 9,924,904 B2 | 3/2018 | Cong et al. |
| 9,925,381 B2 | 3/2018 | Nassif |
| 9,931,513 B2 | 4/2018 | Kelsch et al. |
| 9,931,514 B2 | 4/2018 | Frysz et al. |
| 9,950,171 B2 | 4/2018 | Johanek et al. |
| 9,974,108 B2 | 5/2018 | Polefko |
| 9,974,949 B2 | 5/2018 | Thompson et al. |
| 9,981,121 B2 | 5/2018 | Seifert et al. |
| 9,981,137 B2 | 5/2018 | Eiger |
| 9,987,493 B2 | 6/2018 | Torgerson et al. |
| 9,993,650 B2 | 6/2018 | Seitz et al. |
| 9,999,765 B2 | 6/2018 | Stevenson |
| 10,004,910 B2 | 6/2018 | Gadagkar et al. |
| 10,016,596 B2 | 7/2018 | Stevenson et al. |
| 10,027,157 B2 | 7/2018 | Labbe et al. |
| 10,045,764 B2 | 8/2018 | Scott et al. |
| 10,046,164 B2 | 8/2018 | Gerber |
| 10,047,782 B2 | 8/2018 | Sage et al. |
| 10,052,490 B2 | 8/2018 | Kaula et al. |
| 10,065,044 B2 | 9/2018 | Sharma et al. |
| 10,071,247 B2 | 9/2018 | Childs |
| 10,076,661 B2 | 9/2018 | Wei et al. |
| 10,076,667 B2 | 9/2018 | Kaula et al. |
| 10,083,261 B2 | 9/2018 | Kaula et al. |
| 10,086,191 B2 | 10/2018 | Bonde et al. |
| 10,086,203 B2 | 10/2018 | Kaemmerer |
| 10,092,747 B2 | 10/2018 | Sharma et al. |

(56) References Cited

U.S. PATENT DOCUMENTS

| | | |
|---|---|---|
| 10,092,749 B2 | 10/2018 | Stevenson et al. |
| 10,092,762 B2 | 10/2018 | Jiang et al. |
| 10,095,837 B2 | 10/2018 | Corey et al. |
| 10,099,051 B2 | 10/2018 | Stevenson et al. |
| 10,103,559 B2 | 10/2018 | Cottrill et al. |
| 10,105,542 B2 | 10/2018 | Jiang et al. |
| 10,109,844 B2 | 10/2018 | Dai et al. |
| 10,118,037 B2 | 11/2018 | Kaula et al. |
| 10,124,164 B2 | 11/2018 | Stevenson et al. |
| 10,124,171 B2 | 11/2018 | Kaula et al. |
| 10,124,179 B2 | 11/2018 | Norton et al. |
| 10,141,545 B2 | 11/2018 | Kraft et al. |
| 10,173,062 B2 | 1/2019 | Parker |
| 10,179,241 B2 | 1/2019 | Walker et al. |
| 10,179,244 B2 | 1/2019 | LeBaron et al. |
| 10,183,162 B2 | 1/2019 | Johnson et al. |
| 10,188,857 B2 | 1/2019 | North et al. |
| 10,195,419 B2 | 2/2019 | Shiroff et al. |
| 10,206,710 B2 | 2/2019 | Kern et al. |
| 10,213,229 B2 | 2/2019 | Chitre et al. |
| 10,220,210 B2 | 3/2019 | Walker et al. |
| 10,226,617 B2 | 3/2019 | Finley et al. |
| 10,226,636 B2 | 3/2019 | Gaddam et al. |
| 10,236,709 B2 | 3/2019 | Decker et al. |
| 10,238,863 B2 | 3/2019 | Gross et al. |
| 10,238,877 B2 | 3/2019 | Kaula et al. |
| 10,244,956 B2 | 4/2019 | Kane |
| 10,245,434 B2 | 4/2019 | Kaula et al. |
| 10,258,800 B2 | 4/2019 | Perryman et al. |
| 10,265,532 B2 | 4/2019 | Carcieri et al. |
| 10,277,055 B2 | 4/2019 | Peterson et al. |
| 10,293,168 B2 | 5/2019 | Bennett et al. |
| 10,328,253 B2 | 6/2019 | Wells |
| 10,363,419 B2 | 7/2019 | Simon et al. |
| 10,369,275 B2 | 8/2019 | Olson et al. |
| 10,369,370 B2 | 8/2019 | Shishilla et al. |
| 10,376,701 B2 | 8/2019 | Kaula et al. |
| 10,384,067 B2 | 8/2019 | Jiang et al. |
| 10,406,369 B2 | 9/2019 | Jiang et al. |
| 10,448,889 B2 | 10/2019 | Gerber et al. |
| 10,456,574 B2 | 10/2019 | Chen et al. |
| 10,471,262 B2 | 11/2019 | Perryman et al. |
| 10,485,970 B2 | 11/2019 | Gerber et al. |
| 10,493,282 B2 | 12/2019 | Caparso et al. |
| 10,493,287 B2 | 12/2019 | Yoder et al. |
| 10,561,835 B2 | 2/2020 | Gerber |
| 10,589,103 B2 | 3/2020 | Mathur et al. |
| 10,729,903 B2 | 8/2020 | Jiang et al. |
| 2002/0002390 A1 | 1/2002 | Fischell et al. |
| 2002/0010498 A1 | 1/2002 | Rigaux et al. |
| 2002/0010499 A1 | 1/2002 | Rigaux et al. |
| 2002/0040185 A1 | 4/2002 | Atalar et al. |
| 2002/0051550 A1 | 5/2002 | Leysieffer |
| 2002/0051551 A1 | 5/2002 | Leysieffer et al. |
| 2002/0055761 A1 | 5/2002 | Mann et al. |
| 2002/0068960 A1 | 6/2002 | Saberski et al. |
| 2002/0077572 A1 | 6/2002 | Fang et al. |
| 2002/0116042 A1 | 8/2002 | Boling |
| 2002/0140399 A1 | 10/2002 | Echarri et al. |
| 2002/0156513 A1 | 10/2002 | Borkan |
| 2002/0169485 A1 | 11/2002 | Pless et al. |
| 2002/0177884 A1 | 11/2002 | Ahn et al. |
| 2003/0028072 A1 | 2/2003 | Fischell et al. |
| 2003/0078633 A1 | 4/2003 | Firlik et al. |
| 2003/0114899 A1 | 6/2003 | Woods et al. |
| 2003/0120323 A1 | 6/2003 | Meadows et al. |
| 2003/0195586 A1 | 10/2003 | Rigaux et al. |
| 2003/0195587 A1 | 10/2003 | Rigaux et al. |
| 2003/0212440 A1 | 11/2003 | Boveja |
| 2004/0098068 A1 | 5/2004 | Carbunaru et al. |
| 2004/0106963 A1 | 6/2004 | Tsukamoto et al. |
| 2004/0158298 A1 | 8/2004 | Gliner et al. |
| 2004/0210290 A1 | 10/2004 | Omar-Pasha |
| 2004/0250820 A1 | 12/2004 | Forsell |
| 2004/0260357 A1 | 12/2004 | Vaughan et al. |
| 2004/0260358 A1 | 12/2004 | Vaughan et al. |
| 2004/0267137 A1 | 12/2004 | Peszynski et al. |
| 2005/0004619 A1 | 1/2005 | Wahlstrand et al. |
| 2005/0004621 A1 | 1/2005 | Boveja et al. |
| 2005/0021108 A1 | 1/2005 | Klosterman et al. |
| 2005/0049648 A1 | 3/2005 | Cohen et al. |
| 2005/0075693 A1 | 4/2005 | Toy et al. |
| 2005/0075694 A1 | 4/2005 | Schmeling et al. |
| 2005/0075696 A1 | 4/2005 | Forsberg et al. |
| 2005/0075697 A1 | 4/2005 | Olson et al. |
| 2005/0075698 A1 | 4/2005 | Phillips et al. |
| 2005/0075699 A1 | 4/2005 | Olson et al. |
| 2005/0075700 A1 | 4/2005 | Schommer et al. |
| 2005/0085743 A1 | 4/2005 | Hacker et al. |
| 2005/0104577 A1 | 5/2005 | Matei et al. |
| 2005/0119713 A1 | 6/2005 | Whitehurst et al. |
| 2005/0182454 A1 | 8/2005 | Gharib et al. |
| 2005/0187590 A1 | 8/2005 | Boveja et al. |
| 2005/0240238 A1 | 10/2005 | Mamo et al. |
| 2005/0267546 A1 | 12/2005 | Parramon et al. |
| 2006/0009816 A1 | 1/2006 | Fang et al. |
| 2006/0016452 A1 | 1/2006 | Goetz et al. |
| 2006/0041283 A1 | 2/2006 | Gelfand et al. |
| 2006/0050539 A1 | 3/2006 | Yang et al. |
| 2006/0142822 A1 | 6/2006 | Tulgar |
| 2006/0149345 A1 | 7/2006 | Boggs, II et al. |
| 2006/0200205 A1 | 9/2006 | Haller |
| 2006/0206166 A1 | 9/2006 | Weiner |
| 2007/0025675 A1 | 2/2007 | Kramer |
| 2007/0032834 A1 | 2/2007 | Gliner et al. |
| 2007/0032836 A1 | 2/2007 | Thrope et al. |
| 2007/0049988 A1 | 3/2007 | Carbunaru et al. |
| 2007/0054804 A1 | 3/2007 | Suty-Heinze |
| 2007/0055318 A1 | 3/2007 | Forsberg et al. |
| 2007/0060980 A1 | 3/2007 | Strother et al. |
| 2007/0073357 A1 | 3/2007 | Rooney et al. |
| 2007/0100388 A1 | 5/2007 | Gerber |
| 2007/0208227 A1 | 9/2007 | Smith et al. |
| 2007/0239224 A1 | 10/2007 | Bennett et al. |
| 2007/0245316 A1 | 10/2007 | Bates et al. |
| 2007/0245318 A1 | 10/2007 | Goetz et al. |
| 2007/0265675 A1 | 11/2007 | Lund et al. |
| 2007/0270921 A1 | 11/2007 | Strother et al. |
| 2007/0276441 A1 | 11/2007 | Goetz |
| 2007/0293914 A1 | 12/2007 | Woods et al. |
| 2008/0027514 A1 | 1/2008 | DeMulling et al. |
| 2008/0065178 A1 | 3/2008 | Kelleher et al. |
| 2008/0065182 A1 | 3/2008 | Strother et al. |
| 2008/0071191 A1 | 3/2008 | Kelleher et al. |
| 2008/0077192 A1 | 3/2008 | Harry et al. |
| 2008/0081958 A1 | 4/2008 | Denison et al. |
| 2008/0132961 A1 | 6/2008 | Jaax et al. |
| 2008/0132969 A1 | 6/2008 | Bennett et al. |
| 2008/0154335 A1 | 6/2008 | Thrope et al. |
| 2008/0161874 A1 | 7/2008 | Bennett et al. |
| 2008/0167694 A1 | 7/2008 | Bolea et al. |
| 2008/0172109 A1 | 7/2008 | Rahman et al. |
| 2008/0177348 A1 | 7/2008 | Bolea et al. |
| 2008/0177365 A1 | 7/2008 | Bolea et al. |
| 2008/0183236 A1 | 7/2008 | Gerber |
| 2008/0215112 A1 | 9/2008 | Firlik et al. |
| 2008/0269740 A1 | 10/2008 | Bonde et al. |
| 2008/0278974 A1 | 11/2008 | Wu |
| 2008/0306325 A1 | 12/2008 | Burnett et al. |
| 2009/0018617 A1 | 1/2009 | Skelton et al. |
| 2009/0036946 A1 | 2/2009 | Cohen et al. |
| 2009/0036951 A1 | 2/2009 | Heruth et al. |
| 2009/0048531 A1 | 2/2009 | McGinnis et al. |
| 2009/0054804 A1 | 2/2009 | Gharib et al. |
| 2009/0076565 A1 | 3/2009 | Surwit |
| 2009/0088816 A1 | 4/2009 | Harel et al. |
| 2009/0105785 A1 | 4/2009 | Wei et al. |
| 2009/0112291 A1 | 4/2009 | Wahlstrand et al. |
| 2009/0118788 A1 | 5/2009 | Firlik et al. |
| 2009/0157141 A1 | 6/2009 | Chiao et al. |
| 2009/0171381 A1 | 7/2009 | Schmitz et al. |
| 2009/0204176 A1 | 8/2009 | Miles et al. |
| 2009/0227829 A1 | 9/2009 | Burnett et al. |
| 2009/0234302 A1 | 9/2009 | Hoendervoogt et al. |

(56) References Cited

U.S. PATENT DOCUMENTS

| | | |
|---|---|---|
| 2009/0259273 A1 | 10/2009 | Figueiredo et al. |
| 2009/0281596 A1 | 11/2009 | King et al. |
| 2009/0287272 A1 | 11/2009 | Kokones et al. |
| 2009/0287273 A1 | 11/2009 | Carlton et al. |
| 2009/0306746 A1 | 12/2009 | Blischak |
| 2010/0023084 A1 | 1/2010 | Gunderson |
| 2010/0036445 A1 | 2/2010 | Sakai et al. |
| 2010/0076254 A1 | 3/2010 | Jimenez et al. |
| 2010/0076534 A1 | 3/2010 | Mock |
| 2010/0100158 A1 | 4/2010 | Thrope et al. |
| 2010/0114259 A1 | 5/2010 | Herregraven et al. |
| 2010/0131030 A1 | 5/2010 | Firlik et al. |
| 2010/0145427 A1 | 6/2010 | Gliner et al. |
| 2010/0152808 A1 | 6/2010 | Boggs, II |
| 2010/0152809 A1 | 6/2010 | Boggs, II |
| 2010/0160712 A1 | 6/2010 | Burnett et al. |
| 2010/0168820 A1 | 7/2010 | Maniak et al. |
| 2010/0204538 A1 | 8/2010 | Burnett et al. |
| 2010/0222629 A1 | 9/2010 | Burnett et al. |
| 2010/0222847 A1 | 9/2010 | Goetz |
| 2010/0317989 A1 | 12/2010 | Gharib et al. |
| 2010/0318159 A1 | 12/2010 | Aghassian et al. |
| 2011/0004264 A1 | 1/2011 | Siejko et al. |
| 2011/0054562 A1 | 3/2011 | Gliner |
| 2011/0071593 A1 | 3/2011 | Parker et al. |
| 2011/0125214 A1 | 5/2011 | Goetz et al. |
| 2011/0137378 A1 | 6/2011 | Klosterman et al. |
| 2011/0144468 A1 | 6/2011 | Boggs et al. |
| 2011/0152959 A1 | 6/2011 | Sherwood et al. |
| 2011/0152987 A1 | 6/2011 | Wahlgren et al. |
| 2011/0208263 A1 | 8/2011 | Balzer et al. |
| 2011/0238136 A1 | 9/2011 | Bourget et al. |
| 2011/0251662 A1 | 10/2011 | Griswold et al. |
| 2011/0257701 A1 | 10/2011 | Strother et al. |
| 2011/0278948 A1 | 11/2011 | Forsell |
| 2011/0282416 A1 | 11/2011 | Hamann et al. |
| 2011/0301662 A1 | 12/2011 | Bar-Yoseph et al. |
| 2011/0301667 A1 | 12/2011 | Olson et al. |
| 2011/0313268 A1 | 12/2011 | Kokones et al. |
| 2012/0016447 A1 | 1/2012 | Zhu et al. |
| 2012/0022611 A1 | 1/2012 | Firlik et al. |
| 2012/0029382 A1 | 2/2012 | Kelleher et al. |
| 2012/0041512 A1 | 2/2012 | Weiner |
| 2012/0046712 A1 | 2/2012 | Woods et al. |
| 2012/0071950 A1 | 3/2012 | Archer |
| 2012/0095529 A1 | 4/2012 | Parramon et al. |
| 2012/0101537 A1 | 4/2012 | Peterson et al. |
| 2012/0109258 A1 | 5/2012 | Cinbis et al. |
| 2012/0116741 A1 | 5/2012 | Choi et al. |
| 2012/0119698 A1 | 5/2012 | Karalis et al. |
| 2012/0130448 A1 | 5/2012 | Woods et al. |
| 2012/0136413 A1 | 5/2012 | Bonde et al. |
| 2012/0165899 A1 | 6/2012 | Gliner |
| 2012/0197338 A1 | 8/2012 | Su et al. |
| 2012/0197370 A1 | 8/2012 | Kim et al. |
| 2012/0215285 A1 | 8/2012 | Tahmasian et al. |
| 2012/0238893 A1 | 9/2012 | Farquhar et al. |
| 2012/0253422 A1 | 10/2012 | Thacker et al. |
| 2012/0253442 A1 | 10/2012 | Gliner et al. |
| 2012/0259381 A1 | 10/2012 | Smith et al. |
| 2012/0262108 A1 | 10/2012 | Olson et al. |
| 2012/0265267 A1 | 10/2012 | Blum et al. |
| 2012/0271376 A1 | 10/2012 | Kokones et al. |
| 2012/0271382 A1 | 10/2012 | Arcot-Krishnamurthy et al. |
| 2012/0274270 A1 | 11/2012 | Dinsmoor et al. |
| 2012/0276854 A1 | 11/2012 | Joshi et al. |
| 2012/0276856 A1 | 11/2012 | Joshi et al. |
| 2012/0277621 A1 | 11/2012 | Gerber et al. |
| 2012/0277828 A1 | 11/2012 | O'Connor et al. |
| 2012/0277839 A1 | 11/2012 | Kramer et al. |
| 2012/0290055 A1 | 11/2012 | Boggs, II |
| 2012/0296395 A1 | 11/2012 | Hamann et al. |
| 2012/0310299 A1 | 12/2012 | Kaula et al. |
| 2012/0316630 A1 | 12/2012 | Firlik et al. |
| 2013/0004925 A1 | 1/2013 | Labbe et al. |
| 2013/0006325 A1 | 1/2013 | Woods et al. |
| 2013/0006330 A1 | 1/2013 | Wilder et al. |
| 2013/0006331 A1 | 1/2013 | Weisgarber et al. |
| 2013/0023958 A1 | 1/2013 | Fell |
| 2013/0041430 A1 | 2/2013 | Wang et al. |
| 2013/0072998 A1 | 3/2013 | Su et al. |
| 2013/0079840 A1 | 3/2013 | Su et al. |
| 2013/0096641 A1 | 4/2013 | Strother et al. |
| 2013/0096651 A1 | 4/2013 | Ozawa et al. |
| 2013/0123568 A1 | 5/2013 | Hamilton et al. |
| 2013/0131755 A1 | 5/2013 | Panken et al. |
| 2013/0148768 A1 | 6/2013 | Kim |
| 2013/0150925 A1 | 6/2013 | Vamos et al. |
| 2013/0165814 A1 | 6/2013 | Kaula et al. |
| 2013/0165991 A1 | 6/2013 | Kim et al. |
| 2013/0172956 A1 | 7/2013 | Goddard et al. |
| 2013/0178758 A1 | 7/2013 | Kelleher et al. |
| 2013/0184773 A1 | 7/2013 | Libbus et al. |
| 2013/0197608 A1 | 8/2013 | Eiger |
| 2013/0207863 A1 | 8/2013 | Joshi |
| 2013/0211479 A1 | 8/2013 | Olson et al. |
| 2013/0226261 A1 | 8/2013 | Sparks et al. |
| 2013/0245719 A1 | 9/2013 | Zhu et al. |
| 2013/0245722 A1 | 9/2013 | Ternes et al. |
| 2013/0261684 A1 | 10/2013 | Howard |
| 2013/0261692 A1 | 10/2013 | Cardinal et al. |
| 2013/0283030 A1 | 10/2013 | Drew |
| 2013/0289659 A1 | 10/2013 | Nelson et al. |
| 2013/0289664 A1 | 10/2013 | Johanek |
| 2013/0289665 A1 | 10/2013 | Marnfeldt et al. |
| 2013/0303828 A1 | 11/2013 | Hargrove |
| 2013/0303942 A1 | 11/2013 | Damaser et al. |
| 2013/0310891 A1 | 11/2013 | Enrooth et al. |
| 2013/0310893 A1 | 11/2013 | Yoo et al. |
| 2013/0310894 A1 | 11/2013 | Trier |
| 2013/0325097 A1 | 12/2013 | Loest |
| 2013/0331909 A1 | 12/2013 | Gerber |
| 2013/0345777 A1 | 12/2013 | Feldman et al. |
| 2014/0062900 A1 | 3/2014 | Kaula et al. |
| 2014/0063003 A1 | 3/2014 | Kaula et al. |
| 2014/0063017 A1 | 3/2014 | Kaula et al. |
| 2014/0067006 A1 | 3/2014 | Kaula et al. |
| 2014/0067014 A1 | 3/2014 | Kaula et al. |
| 2014/0067016 A1 | 3/2014 | Kaula et al. |
| 2014/0067354 A1 | 3/2014 | Kaula et al. |
| 2014/0114385 A1 | 4/2014 | Nijhuis et al. |
| 2014/0142549 A1 | 5/2014 | Su et al. |
| 2014/0148870 A1 | 5/2014 | Burnett |
| 2014/0163579 A1 | 6/2014 | Tischendorf et al. |
| 2014/0163580 A1 | 6/2014 | Tischendorf et al. |
| 2014/0163644 A1 | 6/2014 | Scott et al. |
| 2014/0180361 A1 | 6/2014 | Burdick et al. |
| 2014/0180363 A1 | 6/2014 | Zhu et al. |
| 2014/0194771 A1 | 7/2014 | Parker et al. |
| 2014/0194772 A1 | 7/2014 | Single et al. |
| 2014/0194942 A1 | 7/2014 | Sathaye et al. |
| 2014/0194948 A1 | 7/2014 | Strother et al. |
| 2014/0222112 A1 | 8/2014 | Fell |
| 2014/0235950 A1 | 8/2014 | Miles et al. |
| 2014/0236257 A1 | 8/2014 | Parker et al. |
| 2014/0237806 A1 | 8/2014 | Smith et al. |
| 2014/0243931 A1 | 8/2014 | Parker et al. |
| 2014/0249446 A1 | 9/2014 | Gharib et al. |
| 2014/0249599 A1 | 9/2014 | Kaula et al. |
| 2014/0257121 A1 | 9/2014 | Feldman et al. |
| 2014/0277251 A1 | 9/2014 | Gerber et al. |
| 2014/0277268 A1 | 9/2014 | Lee |
| 2014/0277270 A1 | 9/2014 | Parramon et al. |
| 2014/0288374 A1 | 9/2014 | Miles et al. |
| 2014/0288375 A1 | 9/2014 | Miles et al. |
| 2014/0288389 A1 | 9/2014 | Gharib et al. |
| 2014/0296737 A1 | 10/2014 | Parker et al. |
| 2014/0304773 A1 | 10/2014 | Woods et al. |
| 2014/0324144 A1 | 10/2014 | Ye et al. |
| 2014/0343628 A1 | 11/2014 | Kaula et al. |
| 2014/0343629 A1 | 11/2014 | Kaula et al. |
| 2014/0344733 A1 | 11/2014 | Kaula et al. |
| 2014/0344740 A1 | 11/2014 | Kaula et al. |
| 2014/0350636 A1 | 11/2014 | King et al. |

(56) References Cited

U.S. PATENT DOCUMENTS

| | | |
|---|---|---|
| 2014/0379060 A1 | 12/2014 | Hershey |
| 2015/0028798 A1 | 1/2015 | Dearden et al. |
| 2015/0065047 A1 | 3/2015 | Wu et al. |
| 2015/0066108 A1 | 3/2015 | Shi et al. |
| 2015/0088227 A1 | 3/2015 | Shishilla et al. |
| 2015/0094790 A1 | 4/2015 | Shishilla et al. |
| 2015/0100106 A1 | 4/2015 | Shishilla et al. |
| 2015/0123608 A1 | 5/2015 | Dearden et al. |
| 2015/0134027 A1 | 5/2015 | Kaula et al. |
| 2015/0214604 A1 | 7/2015 | Zhao et al. |
| 2015/0231402 A1 | 8/2015 | Aghassian |
| 2015/0360030 A1 | 12/2015 | Cartledge et al. |
| 2016/0045724 A1 | 2/2016 | Lee et al. |
| 2016/0045745 A1 | 2/2016 | Mathur et al. |
| 2016/0045746 A1 | 2/2016 | Jiang et al. |
| 2016/0045747 A1 | 2/2016 | Jiang et al. |
| 2016/0045750 A1 | 2/2016 | Drees et al. |
| 2016/0045751 A1 | 2/2016 | Jiang et al. |
| 2016/0114167 A1 | 4/2016 | Jiang et al. |
| 2016/0121123 A1 | 5/2016 | Jiang et al. |
| 2016/0199659 A1 | 7/2016 | Jiang et al. |
| 2016/0250462 A1 | 9/2016 | Kroll et al. |
| 2017/0007836 A1 | 1/2017 | Nassif |
| 2017/0128728 A1 | 5/2017 | Nassif |
| 2017/0189679 A1 | 7/2017 | Jiang et al. |
| 2017/0197079 A1 | 7/2017 | Illegems et al. |
| 2017/0209703 A1 | 7/2017 | Jiang et al. |
| 2017/0340878 A1 | 11/2017 | Wahlstrand et al. |
| 2018/0000344 A1* | 1/2018 | Melodia ............... H04W 84/18 |
| 2018/0021587 A1 | 1/2018 | Strother et al. |
| 2018/0036477 A1 | 2/2018 | Olson et al. |
| 2018/0117344 A1 | 5/2018 | Mathur et al. |
| 2018/0133491 A1 | 5/2018 | Jiang et al. |
| 2018/0243572 A1 | 8/2018 | Jiang et al. |
| 2018/0333581 A1 | 11/2018 | Nassif |
| 2019/0009098 A1 | 1/2019 | Jiang et al. |
| 2019/0269918 A1 | 9/2019 | Parker |
| 2019/0321645 A1 | 10/2019 | Jiang et al. |
| 2019/0351244 A1 | 11/2019 | Shishilla et al. |
| 2019/0358395 A1 | 11/2019 | Olson et al. |
| 2020/0078594 A1 | 3/2020 | Jiang et al. |

FOREIGN PATENT DOCUMENTS

| | | |
|---|---|---|
| AU | 5123800 | 11/2000 |
| CA | 2371378 | 11/2000 |
| CA | 2554676 | 9/2005 |
| CA | 2957967 | 11/2018 |
| CN | 1745857 | 3/2006 |
| CN | 101495174 | 7/2009 |
| CN | 101626804 | 1/2010 |
| CN | 101721200 | 6/2010 |
| CN | 102164631 | 8/2011 |
| CN | 102176945 | 9/2011 |
| CN | 102202729 | 9/2011 |
| CN | 102215909 | 10/2011 |
| CN | 103002947 | 3/2013 |
| CN | 103079633 | 5/2013 |
| CN | 102307618 | 3/2014 |
| CN | 103796715 | 5/2014 |
| CN | 106999709 | 8/2017 |
| CN | 107073257 | 8/2017 |
| CN | 107078258 | 8/2017 |
| CN | 107148294 | 9/2017 |
| CN | 107427675 | 12/2017 |
| CN | 107073258 | 2/2020 |
| DE | 3146182 | 6/1983 |
| DE | 102010006837 | 8/2011 |
| EP | 0656218 | 6/1995 |
| EP | 1205004 | 5/2002 |
| EP | 1680182 | 7/2006 |
| EP | 1904153 | 4/2008 |
| EP | 2243509 | 10/2010 |
| EP | 1680182 | 5/2013 |
| EP | 1904153 | 4/2015 |
| EP | 3180071 | 6/2017 |
| EP | 3180072 | 6/2017 |
| EP | 3180073 | 6/2017 |
| EP | 3180075 | 6/2017 |
| EP | 3319683 | 5/2018 |
| EP | 3180072 | 11/2018 |
| EP | 3242712 | 4/2019 |
| ES | 2395128 | 2/2013 |
| GB | 1470432 | 4/1977 |
| HK | 1098715 | 3/2012 |
| JP | 048370 | 1/1992 |
| JP | 2003047179 | 2/2003 |
| JP | 2005261662 | 9/2005 |
| JP | 2007505698 | 3/2007 |
| JP | 2007268293 | 10/2007 |
| JP | 4125357 | 7/2008 |
| JP | 2008525089 | 7/2008 |
| JP | 2011529718 | 12/2011 |
| JP | 2013500081 | 1/2013 |
| JP | 2013525017 | 6/2013 |
| JP | 2013541381 | 11/2013 |
| JP | 2013542836 | 11/2013 |
| JP | 2014033733 | 2/2014 |
| JP | 2014514043 | 6/2014 |
| JP | 2017523867 | 8/2017 |
| JP | 2017523868 | 8/2017 |
| JP | 2017523869 | 8/2017 |
| JP | 2017529898 | 10/2017 |
| JP | 2018501024 | 1/2018 |
| JP | 6602371 | 11/2019 |
| KR | 20050119348 | 12/2005 |
| WO | 9639932 | 12/1996 |
| WO | 9820933 | 5/1998 |
| WO | 9918879 | 4/1999 |
| WO | 9934870 | 7/1999 |
| WO | 9942173 | 8/1999 |
| WO | 0002623 | 1/2000 |
| WO | 0019939 | 4/2000 |
| WO | 0019940 | 4/2000 |
| WO | 0056677 | 9/2000 |
| WO | 0001320 | 11/2000 |
| WO | 0065682 | 11/2000 |
| WO | 0066221 | 11/2000 |
| WO | 0069012 | 11/2000 |
| WO | 0078389 | 12/2000 |
| WO | 0183029 | 11/2001 |
| WO | 0193759 | 12/2001 |
| WO | 0203408 | 1/2002 |
| WO | 0209808 | 2/2002 |
| WO | 0137728 | 8/2002 |
| WO | 02072194 | 9/2002 |
| WO | 02072194 | 3/2003 |
| WO | 02078592 | 3/2003 |
| WO | 03026739 | 4/2003 |
| WO | 03043690 | 5/2003 |
| WO | 03005887 | 8/2003 |
| WO | 03035163 | 9/2003 |
| WO | 03066162 | 3/2004 |
| WO | 2004021876 | 3/2004 |
| WO | 2004036765 | 4/2004 |
| WO | 03026482 | 5/2004 |
| WO | 2004047914 | 6/2004 |
| WO | 2004052448 | 6/2004 |
| WO | 2004052449 | 6/2004 |
| WO | 2004058347 | 7/2004 |
| WO | 2004064634 | 8/2004 |
| WO | 2004066820 | 8/2004 |
| WO | 2004087256 | 10/2004 |
| WO | 03037170 | 12/2004 |
| WO | 2004103465 | 12/2004 |
| WO | 2005000394 | 1/2005 |
| WO | 2005002664 | 3/2005 |
| WO | 2005002665 | 6/2005 |
| WO | 2005032332 | 8/2005 |
| WO | 2005079295 | 9/2005 |
| WO | 2005081740 | 9/2005 |
| WO | 2005105203 | 11/2005 |
| WO | 2005123185 | 12/2005 |
| WO | 2006012423 | 2/2006 |

(56) References Cited

FOREIGN PATENT DOCUMENTS

| | | |
|---|---|---|
| WO | 2006019764 | 2/2006 |
| WO | 2005081740 | 3/2006 |
| WO | 2006029257 | 3/2006 |
| WO | 2006091611 | 8/2006 |
| WO | 2006084194 | 10/2006 |
| WO | 2006116256 | 11/2006 |
| WO | 2006119015 | 11/2006 |
| WO | 2006119046 | 11/2006 |
| WO | 2006127366 | 11/2006 |
| WO | 2005087307 | 5/2007 |
| WO | 2007064924 | 6/2007 |
| WO | 2007064936 | 6/2007 |
| WO | 2007108863 | 9/2007 |
| WO | 2007089394 | 11/2007 |
| WO | 2007136694 | 11/2007 |
| WO | 2008021524 | 2/2008 |
| WO | 2008039242 | 4/2008 |
| WO | 2008049199 | 5/2008 |
| WO | 2008042902 | 8/2008 |
| WO | 2008106138 | 9/2008 |
| WO | 2009021080 | 2/2009 |
| WO | 2009042379 | 4/2009 |
| WO | 2009051539 | 4/2009 |
| WO | 2009051965 | 4/2009 |
| WO | 2009042172 | 7/2009 |
| WO | 2009091267 | 7/2009 |
| WO | 2009134478 | 11/2009 |
| WO | 2009137119 | 11/2009 |
| WO | 2009137683 | 11/2009 |
| WO | 2009139907 | 11/2009 |
| WO | 2009139909 | 11/2009 |
| WO | 2009139910 | 11/2009 |
| WO | 2010014055 | 2/2010 |
| WO | 2010014260 | 2/2010 |
| WO | 2009139917 | 3/2010 |
| WO | 2010042056 | 4/2010 |
| WO | 2010042057 | 4/2010 |
| WO | 2010065143 | 6/2010 |
| WO | 2010111321 | 9/2010 |
| WO | 2011011748 | 1/2011 |
| WO | 2011053607 | 5/2011 |
| WO | 2011053661 | 5/2011 |
| WO | 2011059565 | 5/2011 |
| WO | 2011100162 | 8/2011 |
| WO | 2011139779 | 11/2011 |
| WO | 2011153024 | 12/2011 |
| WO | 2012054183 | 4/2012 |
| WO | 2011156286 | 5/2012 |
| WO | 2011156287 | 6/2012 |
| WO | 2012075265 | 6/2012 |
| WO | 2012075281 | 6/2012 |
| WO | 2012075299 | 6/2012 |
| WO | 2012075497 | 6/2012 |
| WO | 2012135733 | 10/2012 |
| WO | 2012155183 | 11/2012 |
| WO | 2012155184 | 11/2012 |
| WO | 2012155185 | 11/2012 |
| WO | 2012155186 | 11/2012 |
| WO | 2012155187 | 11/2012 |
| WO | 2012155188 | 11/2012 |
| WO | 2012155189 | 11/2012 |
| WO | 2012155190 | 11/2012 |
| WO | 2012158766 | 11/2012 |
| WO | 2013028428 | 2/2013 |
| WO | 2013036630 | 3/2013 |
| WO | 2013141884 | 9/2013 |
| WO | 2013141996 | 9/2013 |
| WO | 2013155117 | 10/2013 |
| WO | 2013162709 | 10/2013 |
| WO | 2013165395 | 11/2013 |
| WO | 2014035733 | 3/2014 |
| WO | 2012003451 | 4/2014 |
| WO | 2014087337 | 6/2014 |
| WO | 2014089390 | 6/2014 |
| WO | 2014089392 | 6/2014 |
| WO | 2014089400 | 6/2014 |
| WO | 2014089405 | 6/2014 |
| WO | 2014089485 | 6/2014 |
| WO | 2013162708 | 7/2014 |
| WO | 2014151160 | 9/2014 |
| WO | 2014161000 | 10/2014 |
| WO | 2014172381 | 10/2014 |
| WO | 2016025909 | 2/2016 |
| WO | 2016025912 | 2/2016 |
| WO | 2016025913 | 2/2016 |
| WO | 2016025915 | 2/2016 |
| WO | 2016112398 | 7/2016 |
| WO | 2017011305 | 1/2017 |

OTHER PUBLICATIONS

Bu-802a: How Does Rising Internal Resistance Affect Performance? Understanding the Importance of Low Conductivity, Battery University, Available Online at: https://batteryuniversity.com/learn/article/rising_internal_resistance, Accessed from Internet on May 15, 2020, 10 pages.
DOE Handbook: Primer on Lead-Acid Storage Batteries, United States Department of Energy, Available Online at: htt12s://www.stan dards.doe.gov/standards- documents/ I 000/1084-bhdbk-1995/@@images/file, Sep. 1995, 54 pages.
Medical Electrical Equipment—Part 1: General Requirements for Safety, British Standard, BS EN 60601-1:1990-BS5724-1:1989, Mar. 1979, 200 pages.
Summary of Safety and Effectiveness, Medtronic InterStim System for Urinary Control, Apr. 15, 1999, pp. 1-18.
The Advanced Bionics Precision™ Spinal Cord Stimulator System, Advanced Bionics Corporation, Apr. 27, 2004, pp. 1-18.
UL Standard for Safety for Medical and Dental Equipment, Underwriters Laboratories 544, 4th edition, Dec. 30, 1998, 128 pages.
Barnhart et al., "A Fixed-Rate Rechargeable Cardiac Pacemaker", Applied Physics Laboratory Technical Digest, Jan.-Feb. 1970, pp. 2-9.
Benditt et al., "A Combined Atrial/Ventricular Lead for Permanent Dual-Chamber Cardiac Pacing Applications", Chest, vol. 83, No. 6, Jun. 1983, pp. 929-931.
Boiocchi et al., "Self-Calibration in High Speed Current Steering CMOS D/A Converters", Advanced A-D and D-A Conversion Techniques and their Applications, Second International Conference on Cambridge, Jul. 1994, pp. 148-152.
Bosch et al., "Sacral (S3) Segmental Nerve Stimulation as a Treatment for Urge Incontinence in Patients with Detrusor Instability: Results of Chronic Electrical Stimulation Using an Implantable Neural Prosthesis", The Journal of Urology, vol. 154, No. 2, Aug. 1995, pp. 504-507.
Boyce et al., "Research Related to the Development of an Artificial Electrical Stimulator for the Paralyzed Human Bladder: A Review", The Journal of Urology, vol. 91, No. 1, Jan. 1964, pp. 41-51.
Bradley et al., "Further Experience with the Radio Transmitter Receiver Unit for the Neurogenic Bladder", Journal of Neurosurgery, vol. 20, No. 11, Nov. 1963, pp. 953-960.
Broggi et al., "Electrical Stimulation of the Gasserian Ganglion for Facial Pain: Preliminary Results", Acta Neurochirurgica, vol. 39, 1987, pp. 144-146.
Buhlmann et al., "Modeling of a Segmented Electrode for Desynchronizing Deep Brain Stimulation", Frontiers in Neuroengineering, vol. 4, No. 15, Dec. 8, 2011, 8 pages.
Cameron et al., "Effects of Posture on Stimulation Parameters in Spinal Cord Stimulation", Neuromodulation, vol. 1, No. 4, Oct. 1998, pp. 177-183.
Connelly et al., "Atrial Pacing Leads Following Open Heart Surgery: Active or Passive Fixation?", Pacing and Clinical Electrophysiology, vol. 20, No. 10, Oct. 1997, pp. 2429-2433.
Fischell, "The Development of Implantable Medical Devices at the Applied Physics Laboratory", Johns Hopkins Applied Physics Laboratory Technical Digest, vol. 13 No. 1, 1992, pp. 233-243.
Gaunt et al., "Control of Urinary Bladder Function with Devices: Successes and Failures", Progress in Brain Research, vol. 152, 2006, pp. 1-24.

(56) References Cited

OTHER PUBLICATIONS

Ghovanloo et al., "A Small Size Large Voltage Compliance Programmable Current Source for Biomedical Implantable Microstimulators", Proceedings of the 25th Annual International Conference of the Institute of Electrical and Electronics Engineers, Engineering in Medicine and Biology Society, Sep. 17-21, 2003, pp. 1979-1982.

Gudnason, "A Low-Power ASK Demodulator for Inductively Coupled Implantable Electronics", Solid-State Circuits Conference, 2000, Esscirc 00, Proceedings of the 26rd European, Institute of Electrical and Electronics Engineers, Sep. 19, 2000, pp. 385-388.

Hansen et al., "Urethral Sphincter Emg as Event Detector for Neurogenic Detrusor Overactivity", IEEE Transactions on Biomedical Engineering, vol. 54, No. 7, Jul. 31, 2007, pp. 1212-1219.

Helland, "Technical Improvements to be Achieved by the Year 2000: Leads and Connector Technology", Rate Adaptive Cardiac Pacing, Springer Verlag, 1993, pp. 279-292.

Hidefjall, "The Pace of Innovation—Patterns of Innovation in the Cardiac Pacemaker Industry", Linkoping University Press, 1997, 398 pages.

Ishihara et al., "A Comparative Study of Endocardial Pacemaker Leads", Cardiovascular Surgery, Nagoya Ekisaikai Hospital, 1st Dept. of Surgery, Nagoya University School of Medicine, 1981, pp. 132-135.

Jonas et al., "Studies on the Feasibility of Urinary Bladder Evacuation by Direct Spinal Cord Stimulation. I. Parameters of Most Effective Stimulation", Investigative Urology, vol. 13, No. 2, 1975, pp. 142-150.

Kakuta et al., "In Vivo Long Term Evaluation of Transcutaneous Energy Transmission for Totally Implantable Artificial Heart", American Society for Artificial Internal Organs Journal, Mar.-Apr. 2000, pp. 1-2.

Lazorthes et al., "Chronic Stimulation of the Gasserian Ganglion for Treatment of Atypical Facial Neuralgia", Pacing and Clinical Electrophysiology, vol. 10, Jan.-Feb. 1987, pp. 257-265.

Lewis et al., "Early Clinical Experience with the Rechargeable Cardiac Pacemaker", The Annals of Thoracic Surgery, vol. 18, No. 5, Nov. 1974, pp. 490-493.

Liu et al., "A Neuro-Stimulus Chip with Telemetry Unit for Retinal Prosthetic Device", Institute of Electrical and Electronics Engineers Journal of Solid-State Circuits, vol. 35, No. 10, Oct. 2000, 4 pages.

Love et al., "Experimental Testing of a Permanent Rechargeable Cardiac Pacemaker", The Annals of Thoracic Surgery, vol. 17, No. 2, Feb. 1, 1974, pp. 152-156.

Love, "Pacemaker Troubleshooting and Follow-up", Clinical Cardiac Pacing, Defibrillation, and Resynchronization Therapy, Chapter 24, 2007, pp. 1005-1062.

Madigan et al., "Difficulty of Extraction of Chronically Implanted Tined Ventricular Endocardial Leads", Journal of the American College of Cardiology, vol. 3, No. 3, Mar. 1984, pp. 724-731.

McLennan, "The Role of Electrodiagnostic Techniques in the Reprogramming of Patients with a Delayed Suboptimal Response to Sacral Nerve Stimulation", International Urogynecology Journal, vol. 14, No. 2, Jun. 2003, pp. 98-103.

Meglio, "Percutaneously Implantable Chronic Electrode for Radiofrequency Stimulation of the Gasserian Ganglion. A Perspective in the Management of Trigeminal Pain", Acta Neurochirurgica, vol. 33, 1984, pp. 521-525.

Meyerson, "Alleviation of Atypical Trigeminal Pain by Stimulation of the Gasserian Ganglion via an Implanted Electrode", Acta Neurochirurgica Supplementum, vol. 30, 1980, pp. 303-309.

Mingming, "Development of an Implantable Epidural Spinal Cord Stimulator With Emg Biofeedback", China Master's Theses Fulltext Database: Engineering Technology, vol. 2, No. 6, May 23, 2013, 64 pages.

Mitamura et al., "Development of Transcutaneous Energy Transmission System", Available Online at https://www.researchgate.net/publication/312810915 Ch.28, Jan. 1988, pp. 265-270.

Nag et al., "Flexible Charge Balanced Stimulator With 5.6 fC Accuracy for 140 nC Injections", Institute of Electrical and Electronics Engineers Transactions on Biomedical Circuits and Systems, vol. 7, No. 3, Jun. 2013, pp. 266-275.

Nakamura et al., "Biocompatibility and Practicality Evaluations of Transcutaneous Energy Transmission Unit for the Totally Implantable Artificial Heart System", Journal of Artificial Organs, vol. 27, No. 2, 1998, pp. 347-351.

Nashold et al., "Electromicturition in Paraplegia. Implantation of a Spinal Neuroprosthesis", Archives of Surgery., vol. 104, Feb. 1972, pp. 195-202.

Noblett, "Neuromodulation and the Role of Electrodiagnostic Techniques", International Urogynecology Journal, vol. 21, No. 2, Dec. 2010, 13 pages.

Painter et al., "Implantation of an Endocardial Tined Lead to Prevent Early Dislodgement", The Journal of Thoracic and Cardiovascular Surgery, vol. 77, No. 2, Feb. 1979, pp. 249-251.

Paralikar et al., "A Fully Implantable and Rechargeable Neurostimulation System for Animal Research", 7th Annual International Institute of Electrical and Electronics Engineers Engineering in Medicine and Biology Society, Conference of Neural Engineering, Apr. 22-24, 2015, pp. 418-421.

Perez, "Lead-Acid Battery State of Charge vs. Voltage", Available Online at http://www.rencobattery.com/resources/SOC vs-Voltage.pdf, Aug.-Sep. 1993, 5 pages.

Schaldach et al., "A Long-Lived, Reliable, Rechargeable Cardiac Pacemaker", Engineering in Medicine, vol. 1: Advances in Pacemaker Technology, 1975, 34 pages.

Scheuer-Leeser et al., "Polyurethane Leads: Facts and Controversy", PACE, vol. 6, Mar.-Apr. 1983, pp. 454-458.

Sivaprakasam et al., "A Variable Range Bi-Phasic Current Stimulus Driver Circuitry for an Implantable Retinal Prosthetic Device", Institute of Electrical and Electronics Engineers Journal of Solid-State Circuits, Institute of Electrical and Electronics Engineers Service Center, Piscataway, vol. 40, No. 3, Mar. 1, 2005, pp. 763-771.

Smith, "Changing Standards for Medical Equipment", UL 544 and UL 187 vs. UL 2601 ("Smith"), 2002, 8 pages.

Tanagho et al., "Bladder Pacemaker: Scientific Basis and Clinical Future", Urology, vol. 20, No. 6, Dec. 1982, pp. 614-619.

Tanagho, "Neuromodulation and Neurostimulation: Overview and Future Potential", Translational Androl Urol, vol. 1, No. 1, 2012, pp. 44-49.

Torres et al., "Electrostatic Energy-Harvesting and Battery-Charging CMOS System Prototype", IEEE Transactions on Circuits and Systems I: Regular Papers, vol. 56, No. 9, Dec. 22, 2008, pp. 1938-1948.

Van Paemel, "High-Efficiency Transmission for Medical Implants", Institute of Electrical and Electronics Engineers Solid-State Circuits Magazine, vol. 3, No. 1, Jan. 1, 2011, pp. 47-59.

Von Arx et al., "A Wireless Single-Chip Telemetry-Powered Neural Stimulation System", Institute of Electrical and Electronics Engineers International Solid-State Circuits Conference, ISSCC99, Session 12, Paper TP 12.6, Feb. 16, 1999, pp. 215-216.

Wang et al., "A 140-dB CMRR Low-Noise Instrumentation Amplifier for Neural Signal Sensing", Asia-Pacific Conference on Circuits and Systems, Institute of Electrical and Electronics Engineers Asia Pacific Conference, Dec. 1, 2006, pp. 696-699.

Young, "Electrical Stimulation of the Trigeminal Nerve Root for the Treatment of Chronic Facial Pain", Journal of Neurosurgery, vol. 83, No. 1, Jul. 1995, pp. 72-78.

U.S. Appl. No. 14/827,067, filed Aug. 14, 2015.
U.S. Appl. No. 14/827,074, filed Aug. 14, 2015.
U.S. Appl. No. 14/827,081, filed Aug. 14, 2015.
U.S. Appl. No. 14/827,095, filed Aug. 14, 2015.
U.S. Appl. No. 14/827,108, filed Aug. 14, 2015.
U.S. Appl. No. 14/991,649, filed Jan. 8, 2016.
U.S. Appl. No. 14/991,752, filed Jan. 8, 2016.
U.S. Appl. No. 14/991,784, filed Jan. 8, 2016.
U.S. Appl. No. 62/038,122, filed Aug. 15, 2014.
U.S. Appl. No. 62/038,131, filed Aug. 15, 2014.
U.S. Appl. No. 62/041,611, filed Aug. 25, 2014.
U.S. Appl. No. 62/101,666, filed Jan. 9, 2015.
U.S. Appl. No. 62/101,782, filed Jan. 9, 2015.
U.S. Appl. No. 62/101,884, filed Jan. 9, 2015.

(56) References Cited

OTHER PUBLICATIONS

U.S. Appl. No. 62/101,888, filed Jan. 9, 2015.
U.S. Appl. No. 62/101,897, filed Jan. 9, 2015.
U.S. Appl. No. 62/101,899, filed Jan. 9, 2015.
U.S. Appl. No. 62/110,274, filed Jan. 30, 2015.
U.S. Appl. No. 62/191,134, filed Jul. 10, 2015.

* cited by examiner

TRAINER FOR A NEUROSTIMULATOR PROGRAMMER AND ASSOCIATED METHODS OF USE WITH A NEUROSTIMULATION SYSTEM

CROSS-REFERENCES TO RELATED APPLICATIONS

The present application claims the benefit of priority of U.S. Provisional Application No. 62/852,875 filed on May 24, 2019; and entitled "TRAINER FOR A NEUROSTIMULATOR PROGRAMMER AND ASSOCIATED METHODS OF USE WITH A NEUROSTIMULATION SYSTEM," the entirety of which is hereby incorporated by reference herein.

FIELD OF THE INVENTION

The present invention relates to neurostimulation treatment systems and associated devices, as well as methods and devices for training clinicians, instructors, or other users of such treatment systems.

BACKGROUND OF THE INVENTION

Treatments with implantable neurostimulation systems have become increasingly common in recent years. While such systems have shown promise in treating a number of conditions, effectiveness of treatment may vary considerably between patients. A number of factors may lead to the very different outcomes that patients experience, and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues. Other approaches may also be employed, for example, with one or more electrodes attached to the skin overlying the target nerve structures, implanted in cuffs around a target nerve, or the like. Regardless, the physician will typically seek to establish an appropriate treatment protocol by varying the electrical stimulation that is applied to the electrodes.

Neurostimulation systems are by their very nature complex and may provide reduced to no benefit to patients if adequate training is not provided to a clinician who is tasked with programming the neurostimulation systems (or to those who are instructing the clinician on how to program the neurostimulation systems). Besides simply reading manuals or viewing videos, adequate training requires practical "hands-on" training. However, training using actual pulse generators may not be feasible, at least in part due to the costs associated with these devices. As such, it would be particularly advantageous to provide systems and methods that can simulate pulse generators. Such devices may be used in place of expensive pulse generators. The resulting low-cost training system may be sufficiently available such that a larger number of clinicians or instructors may be able to have access to practical training for longer periods of time.

BRIEF SUMMARY OF THE INVENTION

The present invention generally relates to neurostimulation treatment systems and associated devices and methods, and in particular to systems and methods for simulating tasks related to neurostimulation procedures. The present invention has particular application to sacral nerve stimulation treatment systems configured to treat bladder and bowel related dysfunctions. It will be appreciated however that the present invention may also be utilized for the treatment of pain or other indications, such as movement or affective disorders, as will be appreciated by one of skill in the art.

In some embodiments, a trainer device may be coupled (wirelessly or via a wired connection) to a neurostimulator programmer (NP). The NP may be a device configured to program or adjust parameters of one or more neurostimulators (for example, an IPG or an EPG). For example the NP may be a clinician programmer. The trainer device may be a device that is configured to simulate the one or more neurostimulators. In some embodiments, the trainer device may transmit simulated neurostimulator information to the NP, wherein the simulated neurostimulator information comprises one or more stimulation parameters or information associated with one or more leads. In some embodiments, the trainer device may transmit a simulated first error information to the NP, wherein the first error information comprises an indication of a first error selected from a plurality of errors. In some embodiments, the trainer device may receive a response-information from the NP corresponding to a user input entered by a user to resolve the first error. In some embodiments, the trainer device may register within a local memory of the trainer device that the first error has been resolved. In some embodiments, the trainer device may have one or more retention pins configured to be secured to one or more open ports of the NP.

In some embodiments, the simulated neurostimulator information may include battery information of a simulated neurostimulator. In some embodiments the simulated neurostimulator information may include simulated current information related to a simulated stimulation program. That is, the simulated current information may include current information corresponding to a stimulation program that is currently ongoing. For example, the simulated current information may include values corresponding to one or more current stimulation parameters; an indication of whether stimulation is currently ON or OFF in the simulated stimulation program; an identification of one or more electrodes that are currently stimulating in the simulated stimulation program; an identification of one or more leads that are currently stimulating in the simulated stimulation program; an identification of one or more electrodes that are configured to be enabled in the simulated stimulation program; an identification of one or more leads that are configured to be enabled in the simulated stimulation program; and/or impedance information indicating a measured impedance. In some embodiments, the simulated neurostimulator information may include treatment data about a simulated treatment history of a simulated patient.

In some embodiments, the trainer device may access a data store of the trainer device, wherein the data store comprises a plurality of errors. The trainer device may select the first error from the plurality of errors. The plurality of errors may be maintained in a predetermined order. The first error may be selected based on this predetermined order. Alternatively, the first error may be selected at random from the plurality of errors. In some embodiments, the plurality of errors may include: a low-battery condition indicating that a battery of the pulse generator is approaching a critically low level; a low-battery condition indicating that a battery of the NP is approaching a critically low level; a disconnected- or faulty-lead condition indicating that a lead may be disconnected or otherwise faulty; an excessive-temperature condition indicating that the simulated neurostimulator is above a respective threshold temperature; and/or an excessive-temperature condition indicating that the NP is above a respective threshold temperature.

In some embodiments, the trainer device may transmit a simulated second error information to the NP. The second error information may include an indication of a second error selected from the plurality of errors. The plurality of errors may be maintained in a predetermined order. The second error may be next in sequence based on the predetermined order from the first error, or may be selected at random.

In some embodiments, the trainer device (or the NP) may receive a mode-selection input for cycling between or among two or more pulse-generator modes, wherein the pulse-generator modes comprise an IPG mode and an EPG mode. The trainer device (or the NP) may select a respective pulse-generator mode associated with the received mode-selection input.

In some embodiments, the trainer device may receive a user input requesting an error simulation. In response to receiving the user input, the trainer device may transmit an instruction to the NP to display a simulation of the first error. In some embodiments, the NP may directly receive the user input, in which case the NP may display the error simulation without further instruction from the trainer device. In some embodiments, the trainer device may turn on an error indicator associated with the trainer device that indicates that an error is being simulated. The trainer device may evaluate a response-information corresponding to one or more user inputs to determine if the corresponding one or more user inputs resolve the first error. In response to determining that the corresponding one or more user inputs resolve the first error, the training device may turn off the error indicator. In some embodiments, the evaluation may be performed by the NP, in which case the NP may send an error-resolution information to the trainer device indicating that the first error has been resolved (if the NP determines that the one or more inputs resolve the error).

In some embodiments, one or more indicators on an interface of the trainer device may be turned on or off. The indicators may include: a stimulation indicator that indicates whether or not the NP has successfully sent a command to the trainer device to turn on patient stimulation; one or more pulse-generator mode indicators that indicate whether the simulation is simulating an IPG or an EPG; or one or more error indicators that indicate whether an error is being simulated.

In some embodiments, the trainer device may include circuitry that includes a first circuitry for simulating the one or more neurostimulators, and a second circuitry for simulating placement of a lead. The second circuitry may include a fixed load that may provide a known resistance. The first circuitry and the second circuitry may be housed on separate circuit boards that are not electrically coupled to each other.

In some embodiments, the trainer device may include a foramen needle stimulation cable and a ground electrode cable, wherein the foramen needle stimulation cable is configured to be connected to a first port of the NP, and wherein the ground electrode cable is configured to be connected to a second port of the NP. The trainer device may receive, at the second circuitry, one or more electrical pulses from the NP, wherein the one or more electrical pulses form a completed circuit comprising the foramen needle stimulation cable, the ground electrode cable, and the fixed load of the second circuitry. The trainer device (or the NP) may measure an impedance of the completed circuit, wherein the impedance is associated with at least the fixed load. In embodiments where the trainer device measures the impedance, the trainer device may transmit, to the NP, information corresponding to the measured impedance.

In some embodiments, the trainer device may include a lead stimulation cable and a ground electrode cable, wherein the lead stimulation cable is configured to be connected to a first port of the NP, and wherein the ground electrode cable is configured to be connected to a second port of the NP. The trainer device may receive, at the second circuitry, one or more electrical pulses from the NP, wherein the one or more electrical pulses form a completed circuit comprising the lead stimulation cable, the ground electrode cable, and the fixed load of the second circuitry. The trainer device (or the NP) may measure an impedance of the completed circuit, wherein the impedance is associated with at least the fixed load. In embodiments where the trainer device measures the impedance, the trainer device may transmit, to the NP, information corresponding to the measured impedance.

In some embodiments, a connection may be established between a trainer device and the NP. Circuitry of the trainer device may transmit information identifying a plurality of potential neurostimulators. Circuitry of the trainer device may receive, from the NP, information corresponding to a user selection input by a user. The user selection input may specify a particular one of the plurality of potential neurostimulators. Circuitry of the trainer device may select the particular one of the plurality of neurostimulators for simulation.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION OF THE INVENTION

Figure 1:
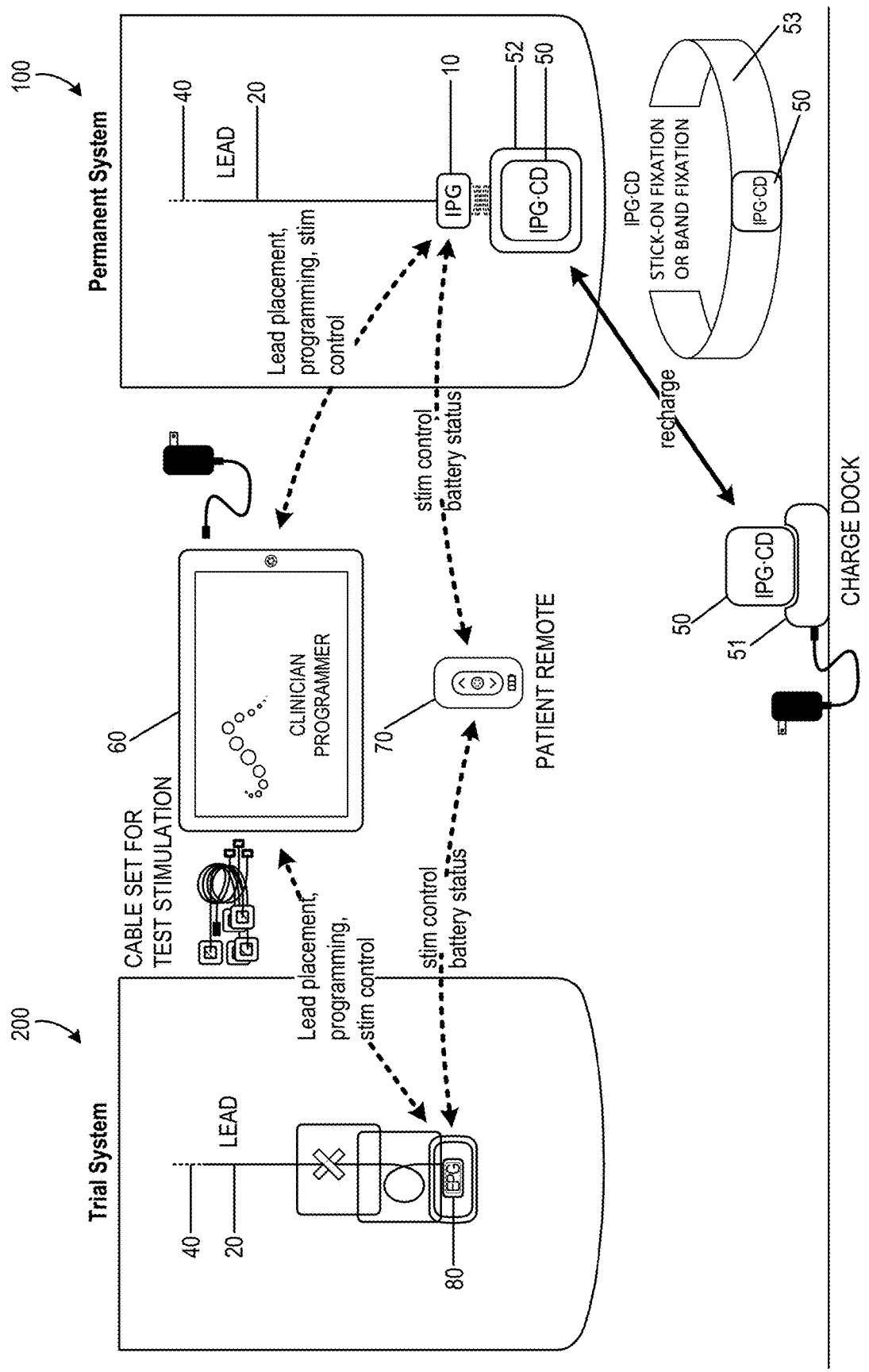
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment, implantation/placement and configuration of such treatment systems. In particular, the invention relates to sacral nerve stimulation treatment systems configured to treat overactive bladder ("OAB") and relieve symptoms of bladder related dysfunction. It will be appreciated however that the present invention may also be utilized for the treatment of pain or other indications, such as movement or affective disorders, as will be appreciated by one of skill in the art.

I. Neurostimulation Indications

Neurostimulation treatment systems, such as any of those described herein, can be used to treat a variety of ailments and associated symptoms, such as acute pain disorders, movement disorders, affective disorders, as well as bladder related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically underrecognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 33 million Americans suffer from OAB. Of the adult population, about 30% of all men and 40% of all women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of Botulinum Toxin (BoNT-A), Percutaneous Tibial Nerve Stimulation (PTNS) and Sacral Nerve Stimulation (SNM). BoNT-A (Botox®) is administered via a series of intradetrusor injections under cystoscopic guidance, but repeat injections of Botox are generally required every 4 to 12 months to maintain effect and Botox may undesirably result in urinary retention. A number or randomized controlled studies have shown some efficacy of BoNT-A in OAB patients, but long-term safety and effectiveness of BoNT-A for OAB is largely unknown.

Alternative treatment methods, typically considered when the above approaches prove ineffective, is neurostimulation of nerves relating to the urinary system. Such neurostimulation methods include PTNS and SNM. PTNS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PTNS has been demonstrated in a few randomized-controlled studies, however, long-term safety and effectiveness of PTNS is relatively unknown at this time.

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG). The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

A. Implantation of Sacral Neuromodulation System

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed percutaneous nerve evaluation and the other is a staged trial.

In percutaneous nerve evaluation, a foramen needle is typically used first to identify the optimal stimulation location, usually at the S3 level, and to evaluate the integrity of the sacral nerves. Motor and sensory responses are used to verify correct needle placement, as described in Table 1 below. A temporary stimulation lead (a unipolar electrode) is then placed near the sacral nerve under local anesthesia. This procedure can be performed in an office setting without fluoroscopy. The temporary lead is then connected to an external pulse generator (EPG) taped onto the skin of the patient during the trial phase. The stimulation level can be adjusted to provide an optimal comfort level for the particular patient. The patient will monitor his or her voiding for 3 to 7 days to see if there is any symptom improvement. The advantage of percutaneous nerve evaluation is that it is an incision free procedure that can be performed in the physician's office using local anesthesia. The disadvantage is that the temporary lead is not securely anchored in place and has the propensity to migrate away from the nerve with physical activity and thereby cause failure of the therapy. If a patient fails this trial test, the physician may still recommend the staged trial as described below. If the percutaneous nerve evaluation trial is positive, the temporary trial lead is removed and a permanent quadri-polar tined lead is implanted along with an IPG under general anesthesia.

Figure 2:
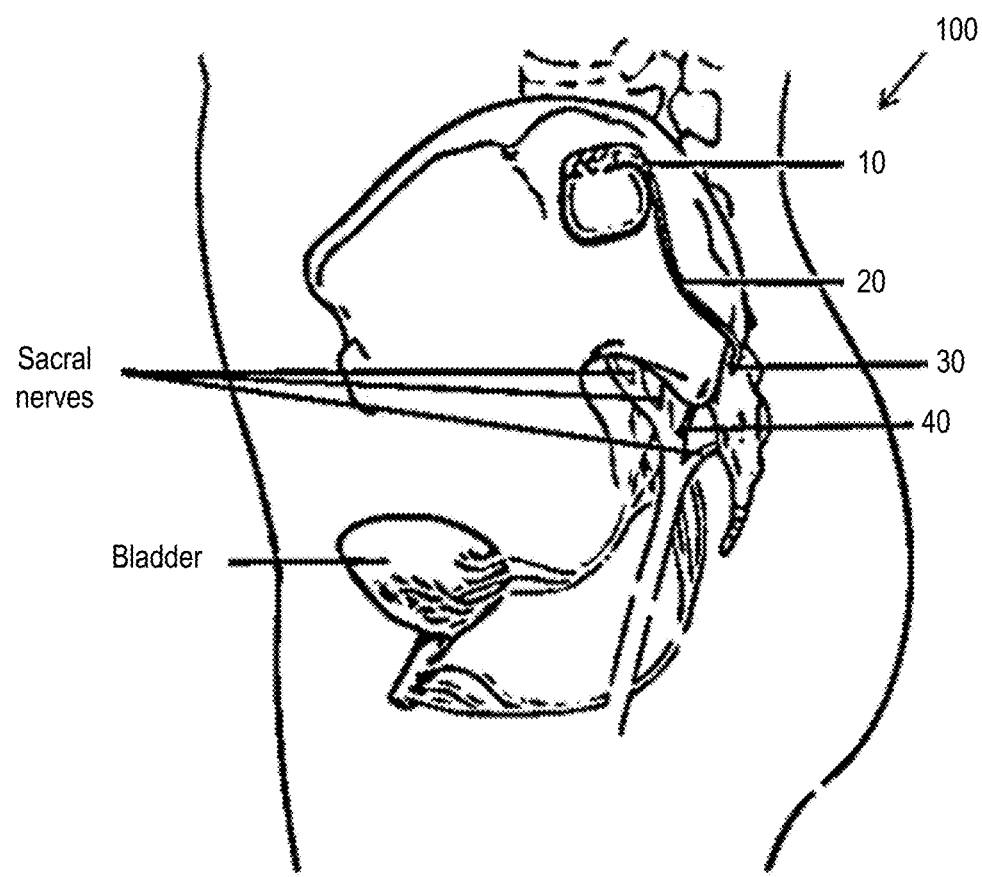
FIG. 2 illustrates an example of a fully implanted neurostimulation system in accordance with aspects of the invention.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIG. 2.

In regard to measuring outcomes for SNM treatment of voiding dysfunction, the voiding dysfunction indications (for example, urge incontinence, urgency-frequency, and non-obstructive urinary retention) are evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day.

The mechanism of action of SNM is multifactorial and impacts the neuro-axis at several different levels. In patients with OAB, it is believed that pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pudendal nerve afferents originating from the pelvic organs into the spinal cord. At the level of the spinal cord, pudendal afferents may turn on voiding reflexes by suppressing exaggerated guarding reflexes, thus relieving symptoms of patients with urinary retention so normal voiding can be facilitated. In patients with fecal incontinence, it is hypothesized that SNM stimulates pudendal afferent somatic fibers that inhibit colonic propulsive activity and activates the internal anal sphincter, which in turn improves the symptoms of fecal incontinence patients. The present invention relates to a system adapted to deliver neurostimulation to targeted nerve tissues in a manner that disrupt, inhibit, or prevent neural activity in the targeted nerve tissues so as to provide therapeutic effect in treatment of OAB or bladder related dysfunction. In one aspect, the system is adapted to provide therapeutic effect by neurostimulation without inducing motor control of the muscles associated with OAB or bladder related dysfunction by the delivered neurostimulation. In another aspect, the system is adapted to provide such therapeutic effect by delivery of sub-threshold neurostimulation below a threshold that induces paresthesia and/or neuromuscular response or to allow adjustment of neurostimulation to delivery therapy at sub-threshold levels.

B. Positioning Neurostimulation Leads with EMG

Placement of the neurostimulation lead may require localization of the targeted nerve and subsequent positioning of the neurostimulation lead at the target location. Various ancillary components are used for localization of the target nerve and subsequent implantation of the lead and IPG. Such components may include a foramen needle and a stylet, a directional guide, dilator and an introducer sheath, straight or curved tip stylet (inserted in tined leads), tunneling tools (a bendable tunneling rod with sharp tip on one end and a handle on the other with a transparent tubing over the tunneling rod) and often an over-the-shelf torque wrench. The foramen needle and stylet may be used for locating the correct sacral foramen for implant lead and subsequent acute stimulation testing. The physician may locate the targeted nerve by inserting a foramen needle and energizing a portion of needle until a neuromuscular response is observed that is indicative of neurostimulation in the target area (see Table 1 above). After the target nerve is successfully located, the direction guide, introducer and dilator may be used to prepare a path along which the lead can be implanted. The directional guide is a metal rod that holds the position in the sacral foramen determined with the foramen needle for subsequent placement of the introducer sheath and dilator. The introducer sheath and dilator is a tool that increases the diameter of the hole through the foramen to allow introduction of the permanent lead. The lead stylet is a stiff wire that is inserted into the lead to increase its stiffness during lead placement and may be configured with a straight or curved tip. The torque wrench is a small wrench used to tighten the set screw that locks the lead into the IPG. The tunneling tool is a stiff, sharp device that creates a subcutaneous tunnel, allowing the lead to be placed along a path under the skin. While such approaches have sufficed for many conventional treatments, such approaches often lack resolution and may result in sub-optimal lead placement, which may unnecessarily complicate subsequent programming and result in unfavorable patient outcomes. Thus, an approach that provides more accurate and robust neural localization while improving ease of use by the physician and the patient.

Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (for example, patient is under general anesthesia).

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, percutaneous nerve evaluation may be done under local anesthesia, using a test needle to identify the appropriate sacral nerve(s) according to a subjective sensory response by the patient. Other testing procedures can involve a two-stage surgical procedure, where a quadri-polar tined lead is implanted for a testing phase to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

In exemplary embodiments, determination of whether or not an implantable lead and neurostimulation electrode is located in a desired or correct location can be accomplished through use of electromyography ("EMG"), also known as surface electromyography. EMG, is a technique that uses an EMG system or module to evaluate and record electrical activity produced by muscles, producing a record called an electromyogram. EMG detects the electrical potential generated by muscle cells when those cells are electrically or neurologically activated. The signals can be analyzed to detect activation level or recruitment order. EMG can be performed through the skin surface of a patient, intramuscularly or through electrodes disposed within a patient near target muscles, or using a combination of external and internal structures. When a muscle or nerve is stimulated by an electrode, EMG can be used to determine if the related muscle is activated, (i.e. whether the muscle fully contracts, partially contracts, or does not contract) in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measureable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measurable muscular reaction can be a partial or a complete muscular contraction, including a response below the triggering of an observable motor response, such as those shown in Table 1, depending on the stimulation of the target muscle. In addition, by utilizing a trial system that allows the neurostimulation lead to remain implanted for use in the permanently implanted system, the efficacy and outcome of the permanently implanted system is more consistent with the results of the trial period, which moreover leads to improved patient outcomes.

C. Example Embodiments of Neurostimulation Systems

FIG. 1 schematically illustrates an exemplary nerve stimulation system, which includes both a trial neurostimulation system 200 and a permanently implanted neurostimulation system 100, in accordance with aspects of the invention. The EPG 80 and IPG 10 are each compatible with and wirelessly communicate with a clinician programmer 60 and a patient remote 70, which are used in positioning and/or programming the trial neurostimulation system 200 and/or permanently implanted system 100 after a successful trial. As discussed above, the clinician programmer can include specialized software, specialized hardware, and/or both, to aid in lead placement, programming, re-programming, stimulation control, and/or parameter setting. In addition, each of the IPG and the EPG allows the patient at least some control over stimulation (for example, initiating a pre-set program, increasing or decreasing stimulation), and/or to monitor battery status with the patient remote. This approach also allows for an almost seamless transition between the trial system and the permanent system.

In one aspect, the clinician programmer 60 is used by a physician to adjust the settings of the EPG and/or IPG while the lead is implanted within the patient. The clinician programmer can be a tablet computer used by the clinician to program the IPG, or to control the EPG during the trial period. The clinician programmer can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the clinician programmer 60 has a control unit which can include a microprocessor and specialized computer-code instructions for implementing methods and systems for use by a physician in deploying the treatment system and setting up treatment parameters. The clinician programmer generally includes a user interface which can be a graphical user interface, an EMG module, electrical contacts such as an EMG input that can couple to an EMG output stimulation cable, an EMG stimulation signal generator, and a stimulation power source. The stimulation cable can further be configured to couple to any or all of an access device (for example, a foramen needle), a treatment lead of the system, or the like. The EMG input may be configured to be coupled with one or more sensory patch electrode(s) for attachment to the skin of the patient adjacent a muscle (for example, a muscle enervated by a target nerve). Other connectors of the clinician programmer may be configured for coupling with an electrical ground or ground patch, an electrical pulse generator (for example, an EPG or an IPG), or the like. As noted above, the clinician programmer can include a module with hardware and computer-code to execute EMG analysis, where the module can be a component of the control unit microprocessor, a pre-processing unit coupled to or in-line with the stimulation and/or sensory cables, or the like.

In some aspects, the clinician programmer is configured to operate in combination with an EPG when placing leads in a patient body. The clinician programmer can be electronically coupled to the EPG during test simulation through a specialized cable set. The test simulation cable set can connect the clinician programmer device to the EPG and allow the clinician programmer to configure, modify, or otherwise program the electrodes on the leads connected to the EPG.

In other aspects, the clinician programmer 60 allows the clinician to read the impedance of each electrode contact whenever the lead is connected to an EPG, an IPG or a clinician programmer 60 to ensure reliable connection is made and the lead is intact. This may be used as an initial step in both positioning the lead and in programming the leads to ensure the electrodes are properly functioning. The clinician programmer 60 is also able to save and display previous (for example, up to the last four) programs that were used by a patient to help facilitate re-programming. In some embodiments, the clinician programmer 60 further includes a USB port for saving reports to a USB drive and a charging port. The clinician programmer 60 is configured to operate in combination with an EPG when placing leads in a patient body as well with the IPG during programming. The clinician programmer 60 can be electronically coupled to the EPG during test simulation through a specialized cable set or through wireless communication, thereby allowing the clinician programmer 60 to configure, modify, or otherwise program the electrodes on the leads connected to the EPG. The clinician programmer 60 may also include physical on/off buttons to turn the clinician programmer 60 on and off and/or to turn stimulation on and off.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

FIG. 2 schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, strength, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 2, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

In one aspect, the EPG unit is wirelessly controlled by a patient remote and/or the clinician programmer in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The clinician programmer can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

Figure 3:
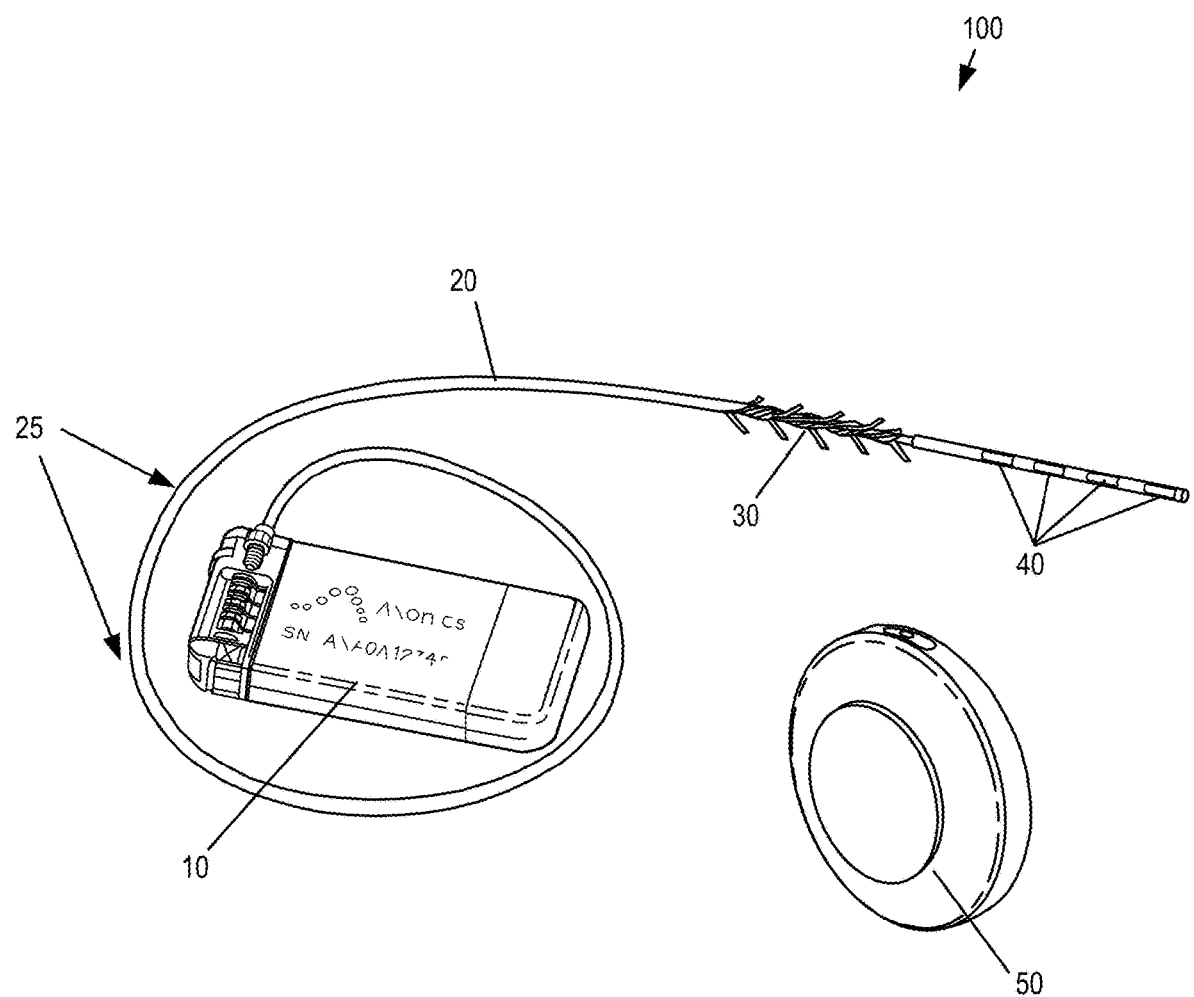
FIG. 3 shows an example of a neurostimulation system having an implantable stimulation lead, an implantable pulse generator, and an external charging device, in accordance with aspects of the invention.

FIG. 3 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes, typically four electrodes. In sacral nerve stimulation, the lead is typically implanted through the S3 foramen as described herein.

Figure 6:
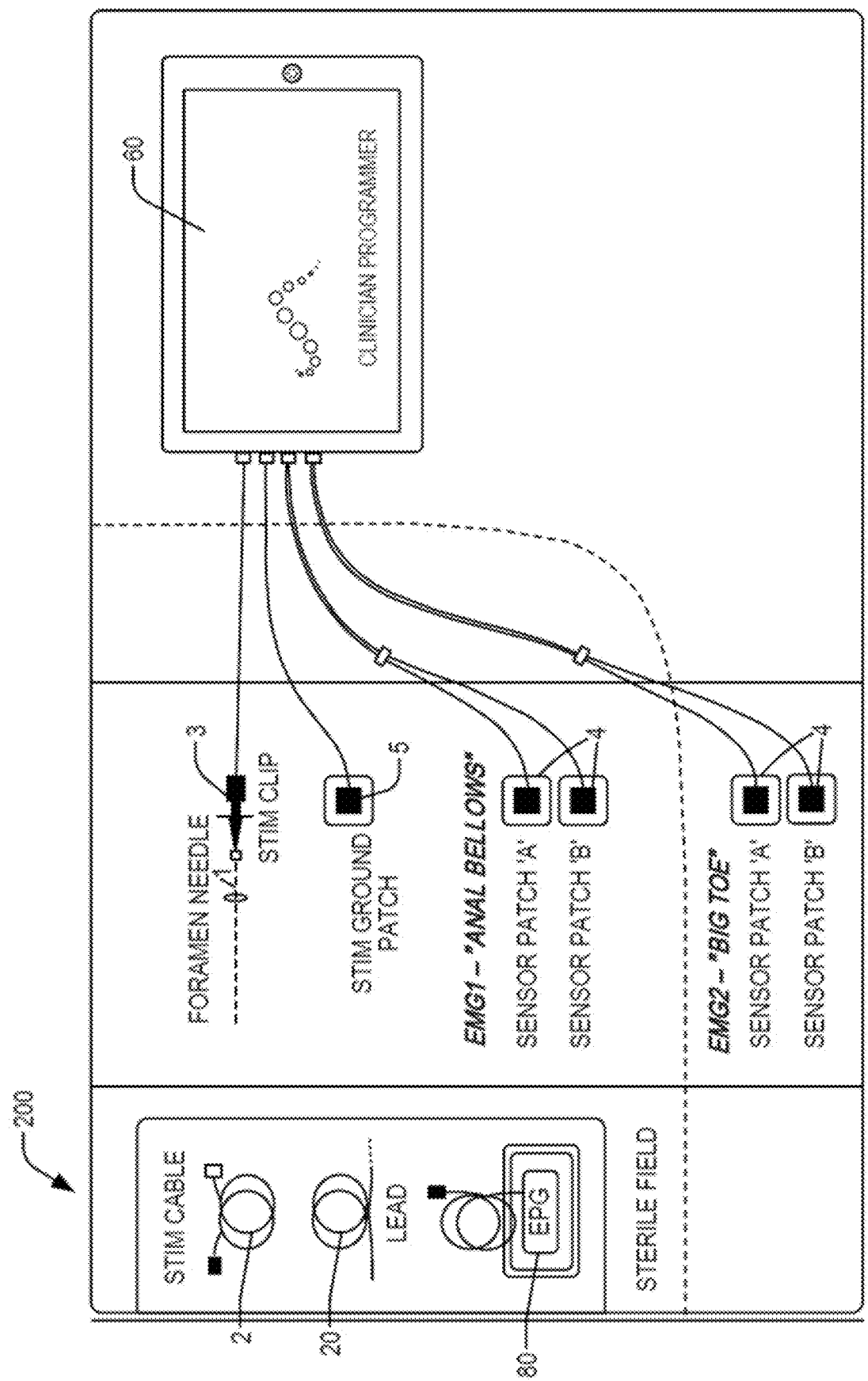
FIG. 6 schematically illustrates a nerve stimulation system utilizing a control unit with a stimulation clip, a ground patch, two electromyography sensors, and ground patch sets connected during the operation of placing a trial or permanent neurostimulation system, in accordance with aspects of the invention.

In one aspect, the IPG is rechargeable wirelessly through conductive coupling by use of a charging device 50 (CD), which is a portable device powered by a rechargeable battery to allow patient mobility while charging. The CD is used for transcutaneous charging of the IPG through RF induction. The CD can either be either patched to the patient's skin using an adhesive or can be held in place using a belt 53 or by an adhesive patch 52, such as shown in the schematic of FIG. 6. The CD may be charged by plugging the CD directly into an outlet or by placing the CD in a charging dock or station 51 that connects to an AC wall outlet or other power source.

The system may further include a patient remote 70 and clinician programmer 60, each configured to wirelessly communicate with the implanted IPG, or with the EPG during a trial, as shown in the schematic of the nerve stimulation system in FIG. 6. The clinician programmer 60 may be a tablet computer used by the clinician to program the IPG and the EPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off.

One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, and typically includes a wireless charging unit.

One or more properties of the electrical pulses can be controlled via a controller of the IPG or EPG. In some embodiments, these properties can include, for example, the frequency, strength, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 10 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 µs to 500 µs, pulse frequency in a range from 5 Hz to 250 Hz, stimulation modes (for example, continuous or cycling), and electrode configuration (for example, anode, cathode, or off), to achieve the optimal therapeutic outcome specific to the patient. In particular, this allows for an optimal setting to be determined for each patient even though each parameter may vary from person to person.

Figure 4:
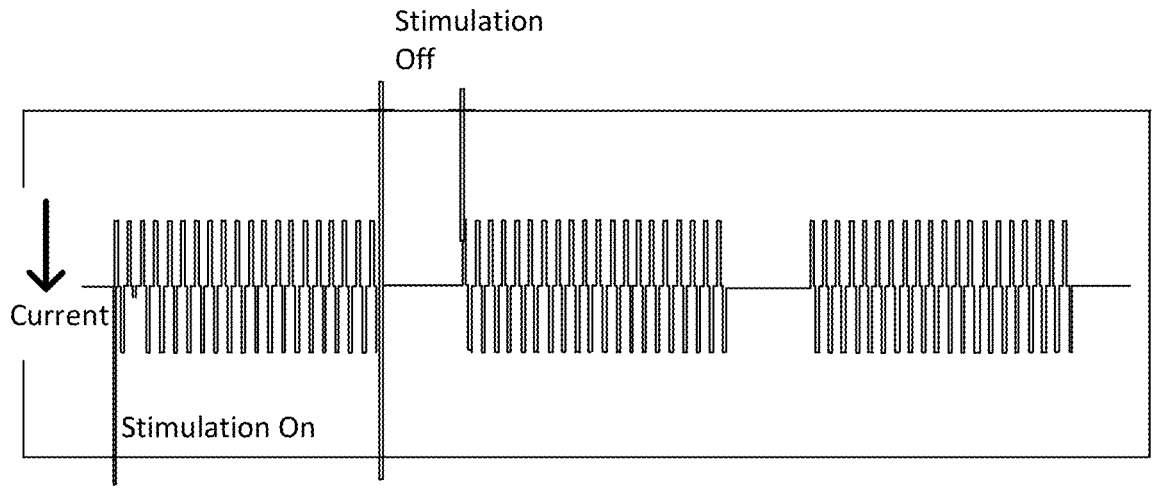
FIG. 4 illustrates an example of stimulation in a cycling mode, in which the duty cycle is the stimulation on time over the stimulation-on time plus the stimulation-off time.

FIG. 4 shows an example of stimulation in a cycling mode, in which the duty cycle is the stimulation on time over the stimulation-on time plus the stimulation-off time. In some embodiments, the IPG, as well as the EPG, may be configured for example with two stimulation modes: continuous mode and cycling mode, such as shown in FIG. 4. The cycling mode may save energy in comparison to the continuous mode, thereby extending the recharge interval of the battery and lifetime of the device. The cycling mode may also help reduce the risk of neural adaptation for some patients. Neural adaptation is a change over time in the responsiveness of the neural system to a constant stimulus. Thus, cycling mode may also mitigate neural adaptation so to provide longer-term therapeutic benefit.

Figure 5:
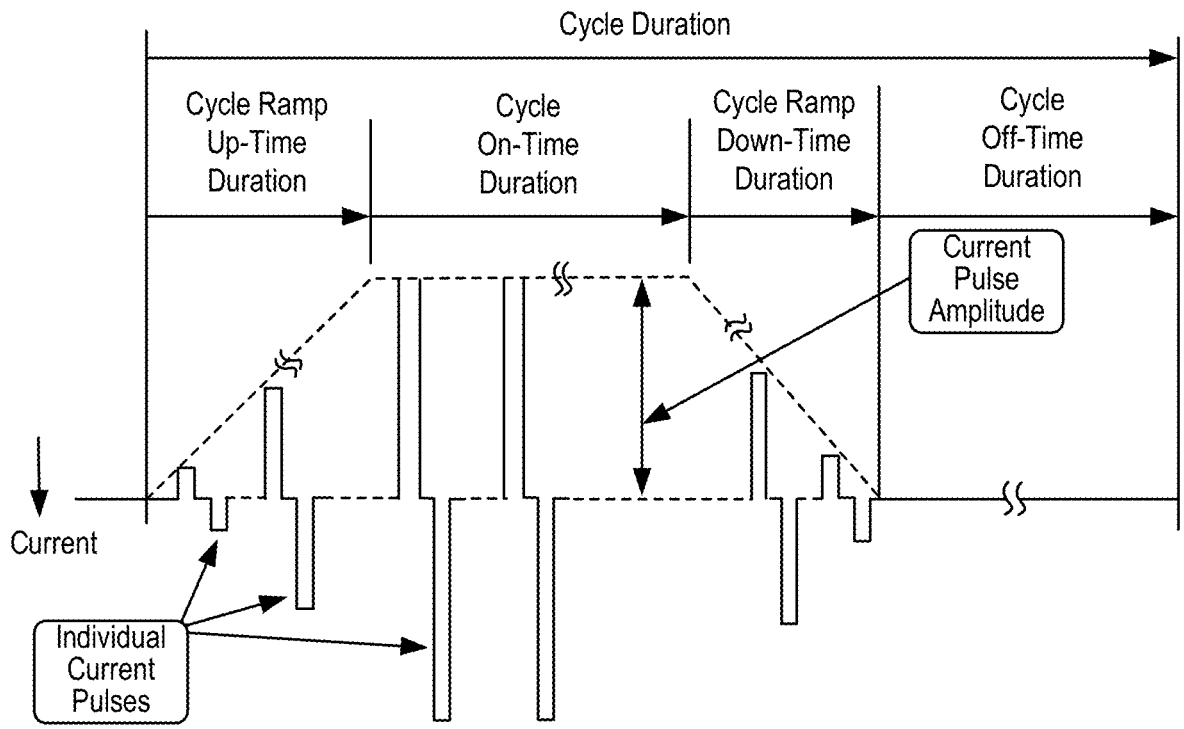
FIG. 5 illustrates signal characteristics of a neurostimulation program, exhibiting a ramping feature.

In some embodiments, the IPG/EPG is configured with a ramping feature, such as shown in the example of FIG. 5. In these embodiments, the stimulation signal is ramped up and/or down between the stimulation-on and stimulation-off levels. This feature helps reduce the sudden "jolting" or "shocking" sensation that some patients might experience when the stimulation is initially turned on or at the cycle-on phase during the cycling mode. This feature is particularly of benefit for patients who need relative high stimulation settings and/or for patients who are sensitive to electrical stimulation.

FIG. 6 shows a setup for a test stimulation and EMG sensing using a clinician programmer 60. As discussed above, the clinician programmer 60 is a tablet computer with software that runs on a standard operating system. The clinician programmer 60 includes a communication module, a stimulation module and an EMG sensing module. The communication module communicates with the IPG and/or EPG in the medical implant communication service frequency band for programming the IPG and/or EPG.

In order to confirm correct lead placement, it is desirable for the physician to confirm that the patient has both adequate motor and sensory responses before transitioning the patient into the staged trial phase or implanting the permanent IPG. However, sensory response is a subjective evaluation and may not always be available, such as when the patient is under general anesthesia. Experiments have shown that demonstrating appropriate motor responses is advantageous for accurate placement, even if sensory responses are available. As discussed above, EMG is a tool which records electrical activity of skeletal muscles. This sensing feature provides an objective criterion for the clinician to determine if the sacral nerve stimulation results in adequate motor response rather than relying solely on subjective sensory criteria. EMG can be used not only to verify optimal lead position during lead placement, but also to provide a standardized and more accurate approach to determine electrode thresholds, which in turn provides quantitative information supporting electrode selection for programming. Using EMG to verify activation of motor responses can further improve the lead placement performance of less experienced operators and allow such physicians to perform lead placement with confidence and greater accuracy.

In one aspect, the system is configured to have EMG sensing capability during re-programming, which can be particularly valuable. Stimulation levels during re-programming are typically low to avoid patient discomfort which often results in difficult generation of motor responses. Involuntary muscle movement while the patient is awake may also cause noise that is difficult for the physician to differentiate. In contrast to conventional approaches, EMG allows the clinician to detect motor responses at very low stimulation levels (for example, sub-threshold), and help them distinguish a motor response originated by sacral nerve stimulation from involuntary muscle movement.

Referring to FIG. 6, several cable sets are connected to the CP. The stimulation cable set consists of one stimulation mini-clip 3 and one ground patch 5. It is used with a foramen needle 1 to locate the sacral nerve and verify the integrity of the nerve via test stimulation. Another stimulation cable set with four stimulation channels 2 is used to verify the lead position with a tined stimulation lead 20 during the staged trial. Both cable sets are sterilizable as they will be in the sterile field. A total of five over-the-shelf sensing electrode patches 4 (for example, two sensing electrode pairs for each sensing spot and one common ground patch) are provided for EMG sensing at two different muscle groups (for example, perineal musculature and big toe) simultaneously during the lead placement procedure. This provides the clinician with a convenient all-in-one setup via the EMG integrated clinician programmer. Typically, only one electrode set (for example, two sensing electrodes and one ground patch) is needed for detecting an EMG signal on the big toe during an initial electrode configuration and/or re-programming session. Typically, these over-the-shelf EMG electrodes are also provided sterile though not all cables are required to be connected to the sterile field. The clinician programmer 60 may allow the clinician to read the impedance of each electrode contact whenever the lead is connected to an EPG, an IPG or a clinician programmer to ensure reliable connection is made and the lead is intact. The clinician programmer 60 is also able to save and display previous (for example, up to the last four) programs that were used by a patient to help facilitate re-programming. In some embodiments, the clinician programmer 60 further includes a USB port for saving reports to a USB drive and a charging port. The clinician programmer may also include physical on/off buttons to turn the clinician programmer on and off and/or to turn stimulation on and off.

Figure 7:
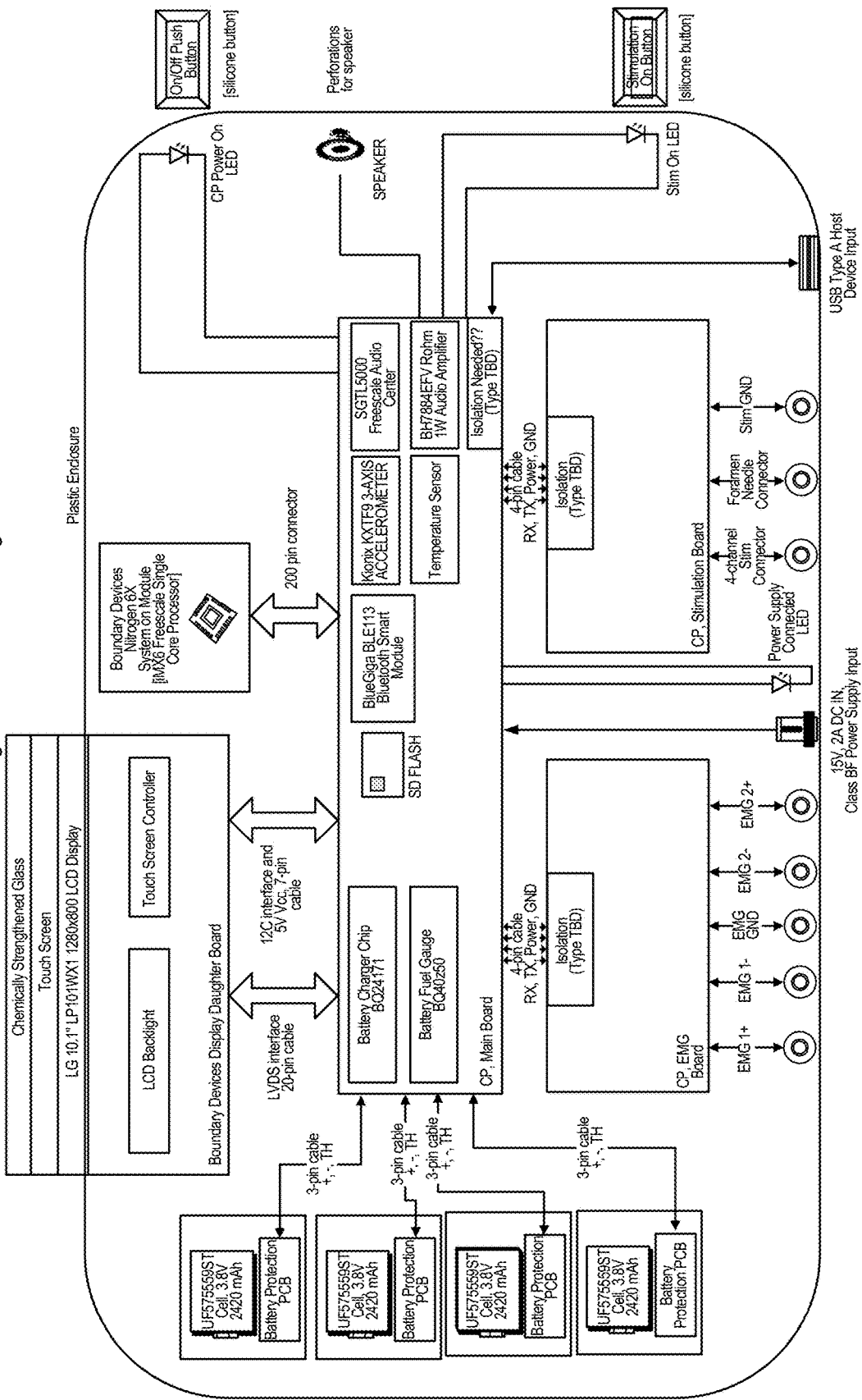
FIG. 7 illustrates a schematic of a clinician programmer configuration.

FIG. 7 schematically illustrates a block diagram of the configuration of the CP 60 and associated interfaces and internal components. As described above, CP 60 is typically a tablet computer with software that runs on a standard operating system. The CP 60 includes a communication module, a stimulation module and an EMG sensing module. The communication module communicates with the IPG and/or EPG in the medical implant communication service frequency band for programming the IPG and/or EPG. While this configuration reflects a portable user interface display device, such as a tablet computer, it is appreciated that the CP may be incorporated into various other types of computing devices, such as a laptop, desktop computer, or a standalone terminal for use in a medical facility.

Figure 8:
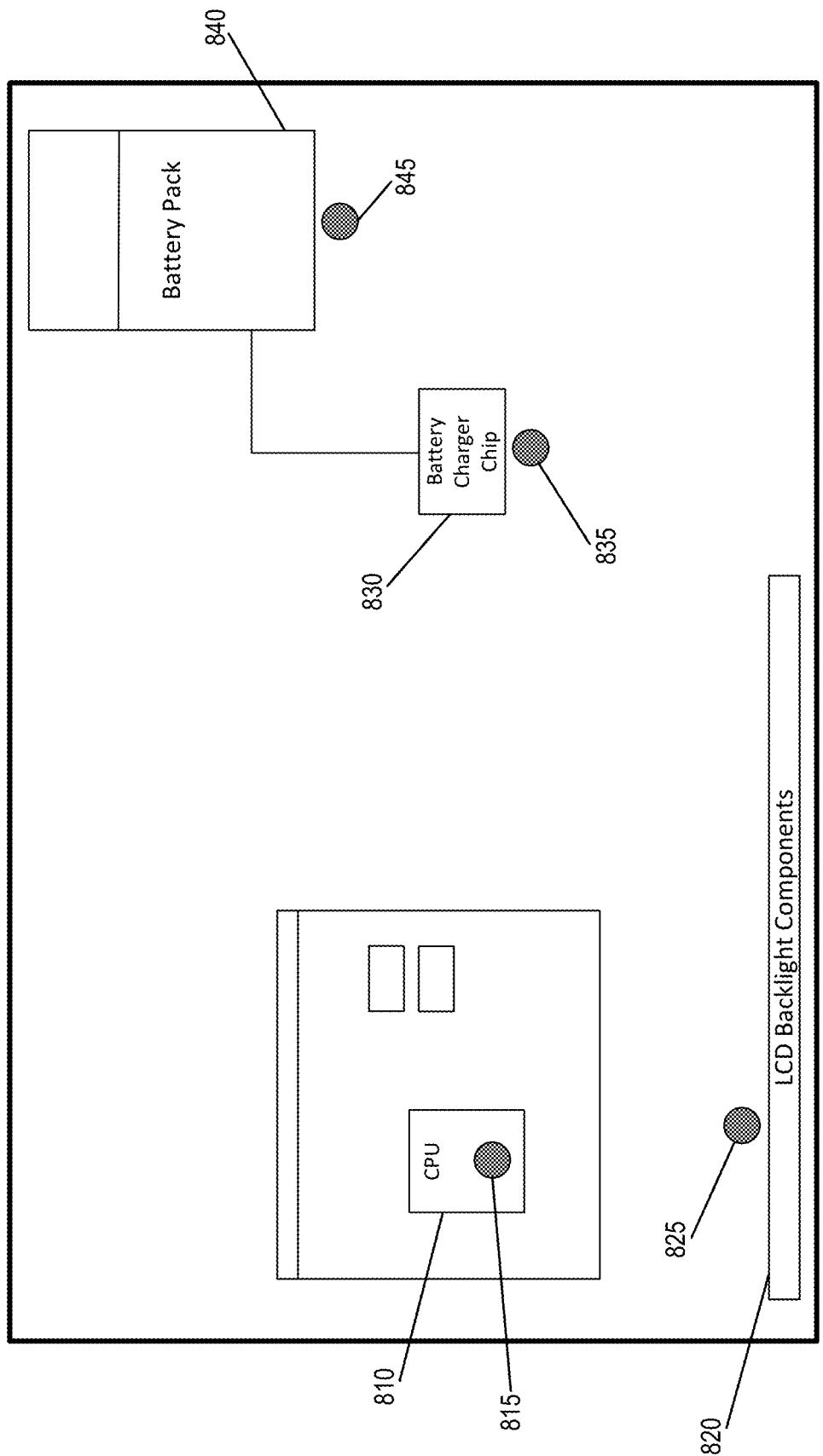
FIG. 8 illustrates an example schematic of a printed circuit board assembly (PCBA) of a neurostimulator programmer including an example set of sensors disposed in example locations.

FIG. 8 illustrates an example schematic of a printed circuit board assembly (PCBA) of a neurostimulator programmer including an example set of sensors disposed in example locations. In some embodiments, the PCBA may include a CPU sensor 815 that may be at or near a CPU 810. The CPU sensor 815 may be located such that it is suited for detecting heat generated by the CPU 810. In some embodiments, the PCBA may include a display sensor 825 that may be at or near one or more backlight components (for example, LCD backlight components 820) of the neurostimulator programmer. The backlight components may include, for example, an inverter and/or LEDs of the backlight. The display sensor 825 may be located such that it is suited for detecting heat generated by the display. In some embodiments, the PCBA may include a charger sensor 835 that may be at or near a charging module (for example, the battery charger chip 830). The charger sensor 835 may be located such that it is suited for detecting heat generated by the charging module as it, for example, steps down voltage, as described elsewhere herein. In some embodiments, the PCBA may include a battery sensor 845 that may be at or near a battery pack 840. The battery pack 840 may include one battery or several batteries that may be coupled together. The battery sensor 845 may be located such that it is suited for detecting heat generated by the charging or discharging of the battery pack 840 or components thereof. Although FIG. 8 illustrates a configuration that includes four different types of sensors (the CPU sensor 815, the display sensor 825, the charger sensor 835, and the battery sensor 845), this disclosure contemplates any number or combination of these types of sensors and/or any other suitable types of sensors. Moreover, although FIG. 8 illustrates only one sensor of each type (for example, only one battery sensor 845, only one display sensor 825) this disclosure contemplates that any suitable number of such sensors may be incorporated into the PCBA. For example, in a case where the battery pack includes four different batteries, there may be a battery sensor 845 adjacent to each of the four different batteries.

III. Trainer for a Neurostimulator Programmer (NP)

In some embodiments, a neurostimulator programmer (NP) may be provided for programming a neurostimulator. The NP may be, for example, the clinician programmer 60, which may be used by a clinician or another suitable operator to program or adjust parameters of one or more neurostimulators. In some embodiments, the programmer may be a patient programmer. The NP may be used to communicate wirelessly with and control either an EPG or an IPG. Alternatively or additionally, the programmer may communicate over a wired connection with the EPG or IPG. Programming a neurostimulator and ensuring proper placement of leads is a complex task that may require extensive hands-on training on the part of a clinician or an instructor (such as an employee of the manufacturer, who may be commissioned to train the clinician). Simply reading a manual for viewing training videos may not provide adequate training. For example, programming a neurostimulator in the real world may involve dealing in real-time with a series of faults or errors that may occur during implantation or programming. As such, a trainer device that may realistically simulate tasks related to the programming of an EPG or IPG is provided for training a user, who may be, for example, a clinician or an instructor. The trainer device may also simulate tasks related to the implantation of leads. For example, the trainer device may simulate one or more checks that may need to be performed to ensure that proper lead placement has occurred. The trainer device may offer an intuitive, easy-to-use means of training users, providing a stimulation that provides conditions very close to what the user would expect in real-world situations. Furthermore, the trainer device may offer an affordable means of training.

Neurostimulator devices such as EPGs and IPGs are by their nature expensive. As such, training users directly with these devices (for example, by connecting the NP to an EPG) is essentially infeasible in many cases, particularly when there are a large number of users to be trained. The trainer device may be manufactured relatively cheaply with simpler components, and may thus offer a cheaper alternative to using expensive EPGs and IPGs for training purposes. The resulting low-cost training system may be sufficiently available such that a larger number of clinicians or instructors may be able to have access to practical training for longer periods of time. Although the disclosure focuses on training clinicians and instructors of clinicians, the disclosure contemplates training devices such as the ones disclosed herein for training patients. For example, the NP may be a patient remote 70.

Figure 9:
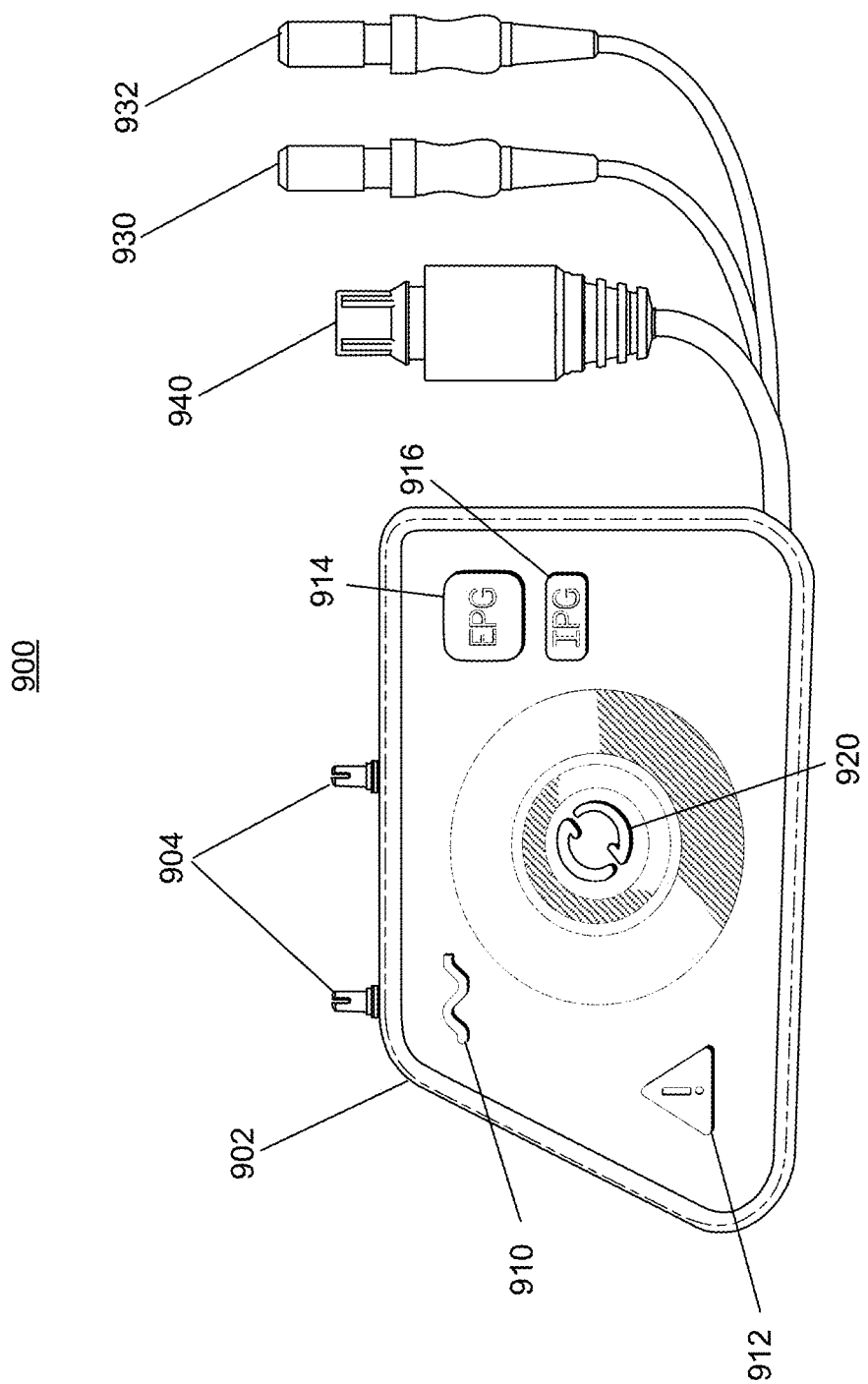
FIG. 9 illustrates an example embodiment of a trainer device showing the structure of a portable housing of the trainer device.

FIG. 9 illustrates an example embodiment of a trainer device 900 showing the structure of a portable housing 902 of the trainer device 900. In some embodiments, the portable housing 902 may have one or more exterior surfaces including one or more interface surfaces. For example, it may have an interface surface on a top side of the exterior surface (this top side is displayed in the example embodiment illustrated in FIG. 9). This interface surface may include one or more switches. For example, the interface surface may include the switch 920, which may be an ON/OFF button that turns the device on or off when pressed or held (for example, turning the device on when pressed and turning the device of when held down for a threshold period of time). Additionally or alternatively, the switch 920 may, for example, be used to cycle between different pulse-generator modes. For example, while the trainer device 900 is on, pressing the switch 920 may cause the trainer device 902 to cycle between an EPG mode and an IPG mode. In some embodiments, the interface surface may include one or more indicators, which may be for example, LEDs or some other suitable light source. For example, the interface surface may include the stimulation indicator 910, which may be a flashing LED that turns on when the NP successfully sends a command to the trainer device 900 to turn on patient stimulation. The LED may turn off when NP sends a command to turn off emulation. As another example, the interface surface may include the IPG indicator 916 which may turn on when the trainer device is turned on and in IPG mode. As another example, the interface surface may include the EPG indicator 914, which may turn on when the trainer device is turned on and in EPG mode. As another example, the interface surface may include a single mode indicator that indicates a current pulse-generator mode (for example, a single indicator that indicates whether the trainer device is in IPG mode or EPG mode). In some embodiments, the interface surface may include an element that is both a switch and an indicator. For example, the interface surface may include the error element 912, which may be an indicator that turns on when a fault status or error is being simulated, as well as a button that may be used to cause the simulation of an error. In this example, the trainer device 900 may send an instruction to the NP to display a simulation of a fault or error. For example, the user may press the error element 912, which may cause the stimulation of a preprogrammed fault. The user may take an appropriate action on the NP to clear the fault or error. If the user action is deemed appropriate, the indicator of the error element 912 may be turned off. In some embodiments, the interface surface may include an element for switching between different simulated stimulation modes (for example, continuous mode and cycling mode).

Figure 10:
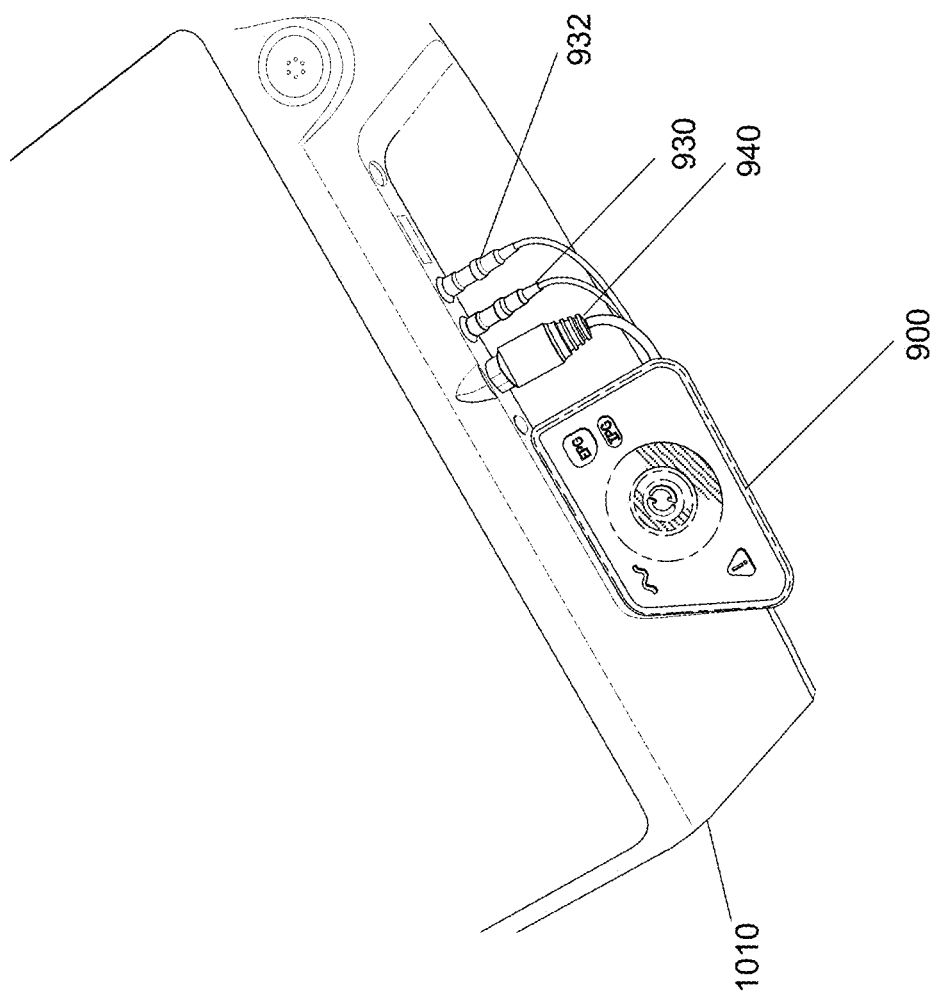
FIG. 10 illustrates an example diagram of the trainer device that is docked onto a NP.

In some embodiments, the trainer device 900 may be configured to be docked onto a NP. FIG. 10 illustrates an example diagram of the trainer device 900 that is docked onto a NP 1010. For example, as shown in FIG. 10, the portable housing 902 of the trainer device 900 may be shaped such that it conforms to a curvature of the NP 1010 (for example, a clinician programmer 60). In some embodiments, the trainer device 900 may include one or more retention pins 904 (for example, as shown in FIG. 9) which may be configured to be fitted into one or more open ports of the NP 1010, or otherwise affixed to the NP 1010, to assist in securing the trainer device 900 to the NP 1010.

In some embodiments, the trainer device 900 may be used to provide a simulation of a neurostimulator programming session. In some embodiments, the user may engage with the simulation via an interface surface of the trainer device 900 and/or a display. The display may be, for example, a display associated with the NP or a display of the trainer device 900 (for example, one that is coupled to the trainer device 900). The display may present a variety of information that may be available to a clinician while programming or monitoring an IPG or EPG in a real-world situation. For example, the display may present a simulated current battery information of a simulated IPG or EPG (for example, voltage, capacity, etc.), status information related to a simulated stimulation program (for example, whether stimulation is on or off, stimulation parameters, an identification of the electrodes and/or leads that are currently stimulating as part of the simulation, an identification of the electrodes and/or leads configured to be enabled in the simulated stimulation program), or impedance information (for example, a simulated impedance provided by tissue around a lead in a real-world situation). The display may also provide information to the user that may require a user action. For example, the display may present one or more simulated faults or errors that may need to be solved by an appropriate action by the user.

In some embodiments, the trainer device 900 may be coupled to a NP. In some embodiments, the NP may be wirelessly coupled (for example, using a wireless network, Bluetooth, near field communication, far field communication) directly or indirectly to the NP. In some embodiments, the user may be able to initiate communication between the trainer device 900 and the NP. For example, the user may be able to "discover" the trainer device 900 on the NP when it is in range (for example, the user may receive a prompt on a display of the NP that the trainer device 900 is in range) and turned on, and may be able to initiate a connection to the trainer device 900 using the NP. As another example, the user may be able to actuate a switch on the trainer device 900, which may cause the trainer device 900 to automatically couple to the NP if it is in range, or send a connection prompt to the NP which may be accepted by the user. The trainer device and the NP may negotiate and establish a connection by any suitable protocols. In other embodiments, the NP may be coupled to the NP via a wired connection.

In some embodiments, the trainer device 900 may transmit simulated neurostimulator information to the NP as part of a simulation of a particular neurostimulator. In some embodiments, the simulated neurostimulator information may include battery information of the simulated neurostimulator. In some embodiments, the simulated neurostimulator information may include one or more stimulation parameters. In some embodiments, the simulated neurostimulator information may include information associated with one or more leads. In some embodiments the simulated neurostimulator information may include simulated current information related to a simulated stimulation program. That is, the simulated current information may include current information corresponding to a stimulation program that is currently ongoing. For example, the simulated current information may include values corresponding to one or more current stimulation parameters; an indication of whether stimulation is currently ON or OFF in the simulated stimulation program; an identification of one or more electrodes that are currently stimulating in the simulated stimulation program; an identification of one or more leads that are currently stimulating in the simulated stimulation program; an identification of one or more electrodes that are configured to be enabled in the simulated stimulation program; an identification of one or more leads that are configured to be enabled in the simulated stimulation program; and/or impedance information indicating a measured impedance. In some embodiments, the simulated neurostimulator information may include treatment data about a simulated treatment history of a simulated patient.

In some embodiments, the trainer device 900 may be configured to simulate a plurality of neurostimulators (for example, neurostimulators of different models and/or manufacturers). In some embodiments, a user of the trainer device 900 may be able to select a particular one of the plurality of neurostimulators to train for that particular neurostimulator. In some embodiments, the selection may be made prior to initiation of a connection between the trainer device 900 and the NP. For example, when the trainer device 900 is in range and turned on, the trainer device 900 may transmit to the NP information identifying a plurality of potential neurostimulators that may be simulated. The user may be presented (for example, on a display of the NP) with a prompt that lists the plurality of potential neurostimulators that may be simulated by the trainer device 900. In this example, the user may submit a selection input at the NP, selecting a particular one of the plurality of potential neurostimulators for training. The NP may then initiate a protocol for connecting to the trainer device 900. The protocol may include a transmission of information corresponding to the user selection to the trainer device 900. In response, the trainer device 900 may negotiate and establish a connection with the NP. From that point on and until instructed otherwise, the trainer device 900 may simulate the particular one of the plurality of potential neurostimulators. In some embodiments, the selection may be made after the connection between the trainer device and the NP is established. For example, the trainer device 900 may transmit to the NP information identifying a plurality of potential neurostimulators that may be simulated after the connection is established. The user may be presented with an initialization prompt that may list the plurality of potential neurostimulators that can be simulated. The initialization prompt may further request that the user select a particular one of the plurality of potential neurostimulators. In this example, the user may submit a selection input at the NP, selecting a particular one of the plurality of potential neurostimulators for training. The NP may transmit information corresponding to the user selection to the trainer device 900. In response, the trainer device 900 may, from that point on and until instructed otherwise, simulate the particular one of the plurality of potential neurostimulators. In particular embodiments, the plurality of potential neurostimulators may be updated at any time via a software update or patch of the trainer device 900. This may be advantageous, for example, because the trainer device 900 may be kept up-to-date and relevant as new models of neurostimulators are developed. In particular embodiments, the plurality of potential neurostimulators may include a plurality of IPGs and/or a plurality of EPGs. In particular embodiments, an interface surface the trainer device 900 may include one or more physical switches or buttons for selecting particular neurostimulators to simulate. For example, an interface surface of the trainer device 900 may include a first button that is dedicated to a first neurostimulator model and the second button that is dedicated to a second neurostimulator model. As another example interface surface of the trainer device 900 may include one or more cycling buttons for cycling through a sequence of different neurostimulator models that may be selected.

In some embodiments, the trainer device 900 may transmit a simulated first error information to the NP. The first error information may include an indication of a first error selected from a plurality of errors. In some embodiments, the plurality of errors may be stored within a data store of the trainer device 900. In some embodiments, the trainer device 900 may access this data store, select the first error, and transmit information about the first error to the NP. In some embodiments, the plurality of errors may be maintained (for example, within the data store of the trainer device 900) in a predetermined order. In these embodiments, the first error may be selected based on the predetermined order. Alternatively, the first error may be selected randomly or pseudo-randomly from the plurality of errors.

In some embodiments, the plurality of errors may include, for example: a low-battery condition indicating that a battery of the pulse generator is approaching a critically low level; a low-battery condition indicating that a battery of the NP is approaching a critically low level; a disconnected- or faulty-lead condition indicating that a lead may be disconnected or otherwise faulty; an excessive-temperature condition indicating that the simulated neurostimulator is above a respective threshold temperature; and/or an excessive-temperature condition indicating that the NP is above a respective threshold temperature.

In some embodiments, the trainer device 900 may transmit an instruction to the NP to display a simulation of an error (for example, the first error). In some embodiments, in response to receiving this instruction, the NP may cause an associated display to, for example, display an indication associated with the error. For example, it may display a message or warning corresponding to the error. Such a message or warning may be identical to or similar to a message or warning that may be displayed in response to a real (that is, non-simulated) error. In some embodiments, the trainer device 900 may also turn on an error indicator (for example, the error element 912) to indicate that an error is being simulated.

In some embodiments, the trainer device 900 may receive a response-information from the NP corresponding to one or more user inputs entered by a user to resolve the first error. In some embodiments, the NP may be configured to receive one or more response-inputs (for example, a user input) from a user in response to the simulation of a particular error. In some embodiments, the response-inputs may associated with a course of action intended to address the particular error. For example, in response to an error indicating an excessive-temperature condition of the IPG, the user may enter a response-input corresponding to reducing a simulated stimulation output or to turning off the IPG. In other embodiments, the response-inputs may simply indicate a confirmation from the user that the error has been acknowledged. For example, a user may enter a confirmation input in response to having received an error indicating a low-battery condition for a simulated IPG. In some embodiments, the response-inputs may be entered at the trainer device 900, for example, at one or more switch elements of the trainer device 900.

In some embodiments, the trainer device 900 may evaluate the response-inputs. That is, the trainer device 900 may evaluate whether the response-inputs from the user adequately address the error being simulated. In doing so, the trainer device 900 may access a memory (for example, a local memory) that may include information about response-inputs that may be appropriate to address each error. In these embodiments, if the trainer device 900 determines that a response-input adequately addresses the error being simulated, the trainer device 900 may register within a local memory of the trainer device 900 that the error has been resolved. If an error element 912 had been turned on due to the error, the trainer device 900 may turn off the error element 912.

In some embodiments, the evaluation of the response-inputs may occur on the NP. That is, the NP may evaluate whether the response-inputs from the user adequately address the error being simulated. In doing so, the NP may access a memory (for example, a local memory) that may include information about response-inputs that may be appropriate to address each error. In these embodiments, if the NP determines that a response-input adequately addresses the error being simulated, the NP may transmit error-resolution information to the trainer device 900, indicating that the first error has been resolved. In response to receiving the error-resolution information, the trainer device 900 may register within a local memory of the trainer device 900 that the error has been resolved. If an error element 912 had been turned on due to the error, the trainer device 900 may turn off the error element 912. In some embodiments, the evaluation may occur partly on the trainer device 900 and partly on the NP.

In some embodiments, the trainer device 900 may transmit a simulated second error information to the NP. The second error information may include an indication of a second error selected from the plurality of errors. In some embodiments, in cases where the plurality of errors is maintained in a predetermined order, the second error may be next in sequence from the first error based on the predetermined order. In some embodiments, the second error may be selected only when it is determined that the first error has been resolved. In other embodiments, the second error may be transmitted only when it is determined that the first error has been resolved, but may be selected before the first error has been resolved.

In some embodiments, the trainer device 900 may receive a mode-selection input for cycling between or among two or more pulse-generator modes. The pulse-generator modes may include an IPG mode and an EPG mode. In response, the trainer device 900 may select a respective pulse-generator mode associated with the received mode selection input. For example, referencing FIG. 9, in the case where the trainer device 900 is currently in an IPG mode, the trainer device 900 may switch from the IPG mode to an EPG mode in response to a user input resulting from a user pressing the switch 920.

In some embodiments, the trainer device 900 may be used to simulate a variety of programming situations other than errors. For example, the trainer device 900 may be used to simulate more ordinary tasks such as the programming of patient stimulation patterns, the programming of modes, the task of switching between modes, the adjusting of parameters, or any other suitable task. Essentially, the trainer device 900 may be used to simulate any tasks that an IPG or EPG may perform.

Figure 11:
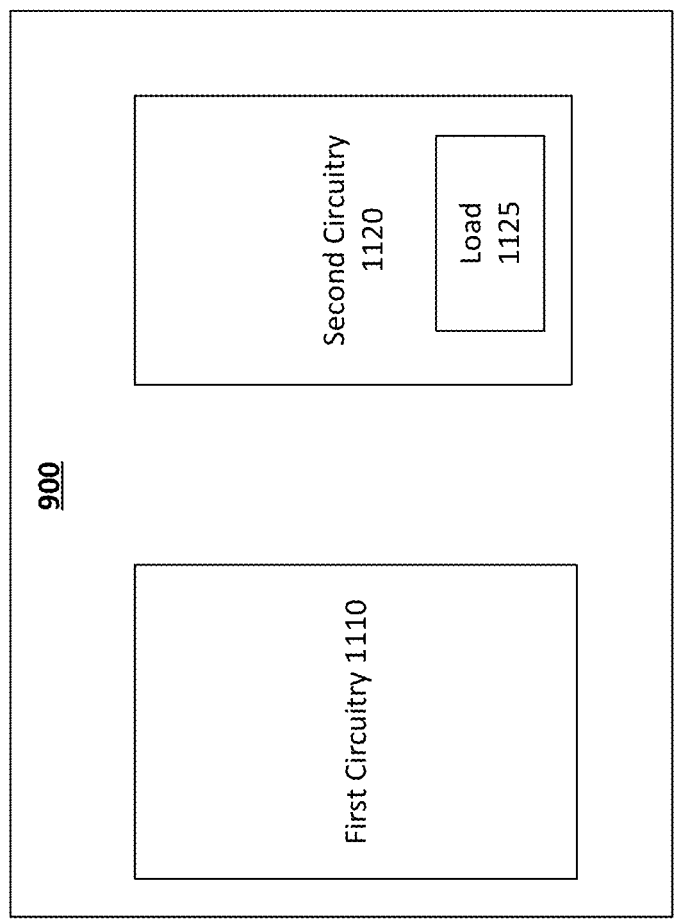
FIG. 11 illustrates a schematic diagram of an example trainer device having separated first and second circuitry.

FIG. 11 illustrates a schematic diagram of an example trainer device 900 having separated first and second circuitry. In some embodiments, referencing FIG. 11, the stimulation of the programming of the neurostimulator may be performed using, at least in part, a first circuitry 1110 of the trainer device 900. In some embodiments, the first circuitry 1110 may include a PCB that may be configured to be coupled (for example, wirelessly or via a wired connection) communicatively to the NP, so that the trainer device 900 and the NP may communicate with each other to generate and display the training simulations described herein.

Figure 12:
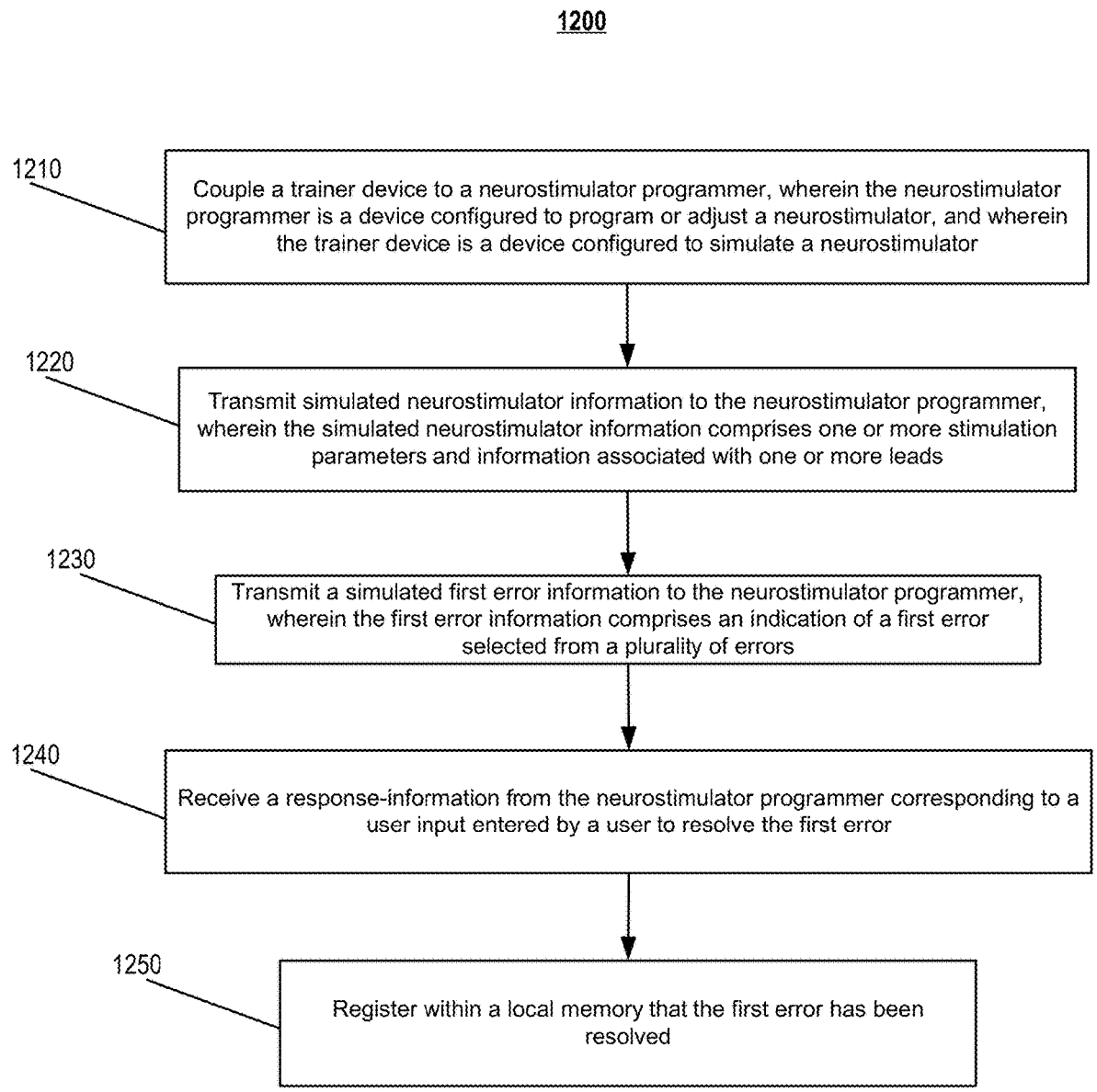
FIG. 12 illustrates an example method for simulating an error during a simulated neurostimulator programming session.

FIG. 12 illustrates an example method 1200 for simulating an error during a simulated neurostimulator programming session. The method may begin at step 1210, where a trainer device may be coupled to a NP, wherein the NP is configured to program or adjust parameters of one or more neurostimulators, and wherein the trainer device is configured to simulate the one or more neurostimulators. At step 1220, the trainer device may transmit simulated neurostimulator information to the NP, wherein the simulated neurostimulator information comprises one or more stimulation parameters or information associated with one or more leads. At step 1230, the trainer device may transmit a simulated first error information to the NP, wherein the first error information comprises an indication of a first error selected from a plurality of errors. At step 1240, the trainer device may receive a response-information from the NP corresponding to a user input entered by a user to resolve the first error. At step 1250, the trainer device may register within a local memory of the trainer device that the first error has been resolved. Particular embodiments may repeat one or more steps of the method of FIG. 12, where appropriate. Although this disclosure describes and illustrates particular steps of the method of FIG. 12 as occurring in a particular order, this disclosure contemplates any suitable steps of the method of FIG. 12 occurring in any suitable order. Moreover, although this disclosure describes and illustrates an example method for simulating an error during a simulated neurostimulator programming session including the particular steps of the method of FIG. 12, this disclosure contemplates any suitable method for simulating an error during a simulated neurostimulator programming session, including any suitable steps, which may include all, some, or none of the steps of the method of FIG. 12, where appropriate. Furthermore, although this disclosure describes and illustrates particular components, devices, or systems carrying out particular steps of the method of FIG. 12, this disclosure contemplates any suitable combination of any suitable components, devices, or systems carrying out any suitable steps of the method of FIG. 12.

Figure 13:
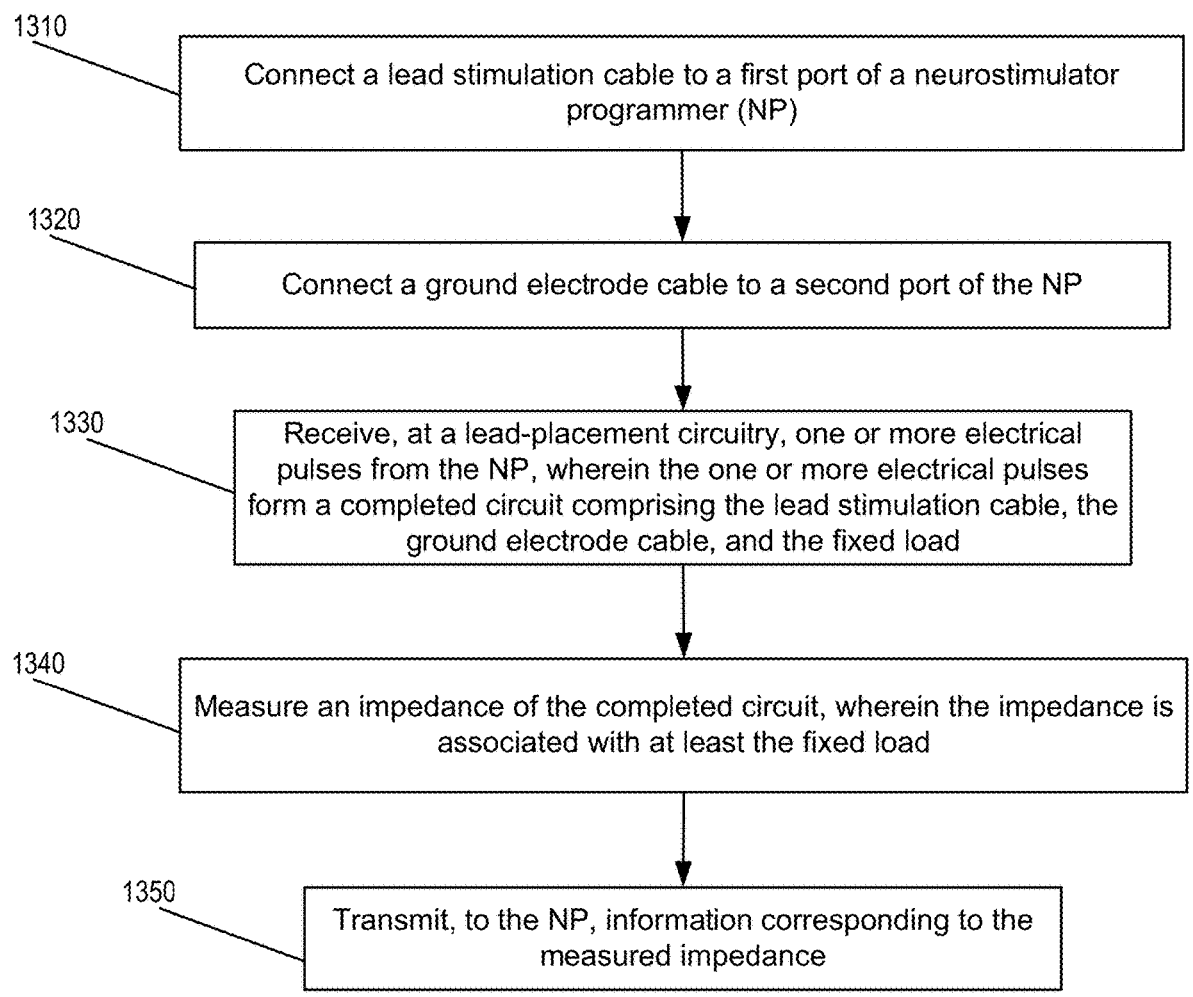
FIG. 13 illustrates an example method for simulating neurostimulation lead placement.

FIG. 13 illustrates an example method 1300 for simulating neurostimulation lead placement. The method may begin at step 1310, where a lead stimulation cable of a neurostimulator training system may be connected to a first port of a NP. At step 1320, a ground of the neurostimulator training system may be connected to a second port of the NP. At step 1330, the lead-placement circuitry of the neurostimulator training system may receive one or more electrical pulses from the NP, wherein the one or more electrical pulses form a completed circuit comprising the lead stimulation cable, the ground electrode cable, and the fixed load. At step 1340, the neurostimulator training system may measure an impedance of the completed circuit, wherein the impedance is associated with at least the fixed load. At step 1350, the neurostimulator training system Particular embodiments may repeat one or more steps of the method of FIG. 13, where appropriate. Although this disclosure describes and illustrates particular steps of the method of FIG. 13 as occurring in a particular order, this disclosure contemplates any suitable steps of the method of FIG. 13 occurring in any suitable order. Moreover, although this disclosure describes and illustrates an example method for simulating neurostimulation lead placement including the particular steps of the method of FIG. 13, this disclosure contemplates any suitable method for simulating neurostimulation lead placement, including any suitable steps, which may include all, some, or none of the steps of the method of FIG. 13, where appropriate. Furthermore, although this disclosure describes and illustrates particular components, devices, or systems carrying out particular steps of the method of FIG. 13, this disclosure contemplates any suitable combination of any suitable components, devices, or systems carrying out any suitable steps of the method of FIG. 13.

In some embodiments, the trainer device 900 may be used to provide a lead placement simulation, which may be a simulation of the checks involved in ensuring proper placement of a lead. One of these checks may include measuring and impedance, which may confirm that a lead has been implanted within tissue, or within a particular type of tissue associated with a signature impedance. For example, a clinician implanting a lead may check to confirm that the lead has been implanted in an area that provides an appropriate impedance value (for example, an impedance value that is within a threshold range of a specified impedance value associated with a target tissue). Alternatively or additionally, an impedance measurement may be used to indicate that a reliable connection has been made between a lead and an IPG or an EPG and/or that the lead is intact. This may be used as an initial step in positioning the lead and/or in programming the leads to ensure the electrodes are properly functioning. In some embodiments, the specified impedance value may be around 500 ohms.

In some embodiments, the lead placement simulation may be provided when the trainer device 900 is operating in a different mode, termed herein as "Lead Placement Mode." In some embodiments, for example referencing FIG. 11, the trainer device 900 may include a second circuitry 1120. In some embodiments, the trainer device 900 may include one or more cables for lead placement simulation. These cables may be configured for connection to the NP. For example, the cables may include a foramen needle stimulation cable 930, a ground electrode cable 932, and a lead stimulation cable 940 for simulating a lead (for example, a cable for simulating a four-channel lead or a five-channel lead). In some embodiments, the NP may include circuitry that is configured to output a pulse with predetermined characteristics (for example, a predetermined voltage) via the cables to a circuit portion 920 within the trainer device 900. The trainer device 900 may include a load 1125 (which may include one or more resistors) within the portable housing 902 that may provide a "dummy" impedance, through which the pulse may travel. In some embodiments, the load 1125 may be part of the second circuitry 1120. The trainer device 900 (or alternatively, the NP to which the trainer device 900 is connected) may be able to confirm the impedance provided by the load. In some embodiments, the second circuitry may be separated from the first circuitry 1110 that is used to simulate the EPG or IPG. For example, the second circuitry 1120 may be disposed at least in part on a separate PCB, and may be isolated from a PCB of the second circuitry 1120. Disposing the second circuitry 1120 on a separate PCB may be advantageous in that such separation of the different circuitries may permit easier modification of the second circuitry 1120 without the risk of affecting the first circuitry 1110. For example, this may allow for easy modification of the load 1125 in the second circuitry 1120 to change the simulated lead impedance values (for example, replacing a 500-ohm resistor that may be in the load 1125 with a 600-ohm resistor). Alternatively, such separation may permit easier modification of the first circuitry 1110 without the risk of affecting the second circuitry 1120.

In some embodiments, the lead placement simulation may include, for example, two phases: (1) the foramen needle insertion phase and (2) the lead insertion phase. The foramen needle insertion phase may simulate the task of inserting a foramen needle into a tissue near a target nerve. In a real medical procedure, the insertion of the foramen needle may be done, for example, to identify the optimal stimulation location, as described elsewhere herein. In some embodiments, referencing FIG. 10, the simulation for the foramen needle insertion phase may involve the user of the trainer device 900 connecting the foramen needle stimulation cable 930 and the ground electrode cable 932 to suitable ports of the NP 1010. For example, the foramen needle stimulation cable 930 may be connected to a first port of the NP 1010 and the ground electrode cable 932 may be connected to a second port of the NP 1010. In some embodiments, following activation of Lead Placement Mode, the NP may output a pulse, completing a circuit that may include the foramen needle stimulation cable 930 and the ground electrode cable 932. The circuit may include the load 1125, which may provide an impedance that simulates a target tissue. In some embodiments, the circuit may also include one or more other fixed loads (for example, a 100-ohm resistor, disposed within the NP, in series with the load 1125 when the circuit is completed). In some embodiments, the trainer device 900 may be able to measure the impedance of the circuit, which includes the impedance provided by the load 1125. For example, the trainer device may receive, at the second circuitry 1120, one or more electrical pulses from the NP, wherein the one or more electrical pulses form a completed circuit that includes at least the foramen needle stimulation cable, the ground electrode cable, and the fixed load of the second circuitry. The trainer device 900 may measure an impedance of the completed circuit, wherein the impedance is associated with at least the fixed load. The trainer device 900 may then transmit, to the NP, information corresponding to the measured impedance. In other embodiments, the NP may make this measurement (that is, the measurement step may occur on the NP).

The impedance measurement may be based on, for example, measuring the voltage differential or the current in the circuit (for example, using Ohm's law, V=IR). As an example, the impedance of the load 1125 may be around 499 ohms. The measured impedance may be around 499 ohms, or alternatively may be higher based on the presence of one or more other fixed loads. For example, the circuit may have a 100-ohm resistor in series with the foramen needle connection and a 100-ohm resistor in series with the ground electrode connection, which may result in a measured impedance of 699 ohms. The measured impedance may be displayed on a display, for example a display associated with the NP 1010 or a display associated with the trainer device 900. The user of the trainer device 900 may be able to view the measured impedance on the display and determine that the simulated foramen needle has been placed in a simulated location that provides the correct impedance.

In the lead insertion phase of the lead placement simulation, the trainer device 900 may simulate the implantation of one or more leads of an IPG or EPG. As an example, FIGS. 9-10 illustrate a configuration that may be used to training for a single lead, the implantation of which may be simulated by the lead stimulation cable 940. The user may connect the ground electrode cable 932 and the lead stimulation cable 940 to suitable ports of the NP 1010. As with the foramen needle insertion phase, the clinician programmer may output a pulse with predetermined characteristics, completing a circuit that includes the ground electrode cable 932 lead stimulation cable 940. The circuit may also include the load 1125. Similar to the foramen needle insertion phase, in some embodiments, the trainer device 900 may be able to measure the impedance of the circuit, which includes the impedance provided by the load 1125. For example, the trainer device may receive, at the second circuitry 1120, one or more electrical pulses from the NP, wherein the one or more electrical pulses form a completed circuit that includes at least the lead stimulation cable, the ground electrode cable, and the fixed load of the second circuitry. The trainer device 900 may measure an impedance of the completed circuit, wherein the impedance is associated with at least the fixed load. The trainer device 900 may then transmit, to the NP, information corresponding to the measured impedance. In other embodiments, again similar to the foramen needle insertion phase, the NP may make this measurement (that is, the measurement step may occur on the NP).

In some embodiments, the circuit for the lead insertion phase may include one or more other fixed loads. For example, the circuit may include a 100-ohm resistor in series with the ground electrode connection. In this example, a load 1125 that has an impedance of 499 ohms may yield measured impedance of 599 ohms. The measured impedance may be displayed, for example, on a display associated with the NP. The user of the trainer device 900 may be able to view the measured impedance on the display and determine that the simulated lead has been placed in a simulated location that provides the correct impedance.

In some embodiments, Lead Placement Mode may be initiated when the user manually activates the mode. For example, the user may activate this mode by actuating an appropriate button on the clinician programmer or the trainer device 900. In some embodiments, this mode may be automatically activated by the trainer device 900 when the user simply plugs in the cables associated with the lead placement mode.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of providing a simulation of a neurostimulator programming session, the method comprising:
    coupling a trainer device to a neurostimulator programmer (NP), wherein the NP is configured to program or adjust parameters of one or more neurostimulators, and wherein the trainer device is configured to simulate the one or more neurostimulators;
    by the circuitry of the trainer device, transmitting a simulated first error information to the NP, wherein the first error information comprises an indication of a first error selected from a plurality of errors; and
    by the circuitry of the trainer device, receiving a response-information from the NP corresponding to a user input entered by a user to resolve the first error.

2. The method of claim 1, wherein the NP is a clinician programmer, and wherein the one or more neurostimulators that the trainer device is configured to simulate comprises an implantable pulse generator (IPG) or an external pulse generator (EPG).

3. The method of claim 1, further comprising transmitting simulated neurostimulator information to the NP, wherein the simulated neurostimulator information comprises battery information of a simulated one of the one or more neurostimulators.

4. The method of claim 1, further comprising transmitting simulated neurostimulator information to the NP, wherein the simulated neurostimulator information comprises simulated current information related to a simulated stimulation program, the current information comprising:
    one or more stimulation parameters;
    an indication of whether stimulation is currently ON or OFF in the simulated stimulation program;
    an identification of one or more electrodes that are currently stimulating in the simulated stimulation program;
    an identification of one or more leads that are currently stimulating in the simulated stimulation program;
    an identification of one or more electrodes that are configured to be enabled in the simulated stimulation program;
    an identification of one or more leads that are configured to be enabled in the simulated stimulation program; or
    impedance information indicating a measured impedance.

5. The method of claim 1, further comprising transmitting simulated neurostimulator information to the NP, wherein the simulated neurostimulator information further comprises treatment data about a simulated treatment history of a simulated patient.

6. The method of claim 1, further comprising:
    accessing a data store of the trainer device, wherein the data store comprises a plurality of errors; and
    selecting the first error from the plurality of errors.

7. The method of claim 6, wherein the plurality of errors is maintained in a predetermined order, and wherein the first error is selected based on the predetermined order.

8. The method of claim 6, wherein the first error is selected at random from the plurality of errors.

9. The method of claim 6, wherein the plurality of errors comprises a low-battery condition indicating that a battery of a simulated one of the one or more neurostimulators is approaching a critically low level.

10. The method of claim 6, wherein the plurality of errors comprises a disconnected- or faulty-lead condition indicating that a lead is disconnected or otherwise faulty.

11. The method of claim 6, wherein the plurality of errors comprises an excessive-temperature condition indicating that a simulated one of the one or more neurostimulators is above a respective threshold temperature, or an excessive-temperature condition indicating that the NP is above a respective threshold temperature.

12. The method of claim 1, further comprising:
transmitting a simulated second error information to the NP, wherein:
the second error information comprises an indication of a second error selected from the plurality of errors,
the plurality of errors is maintained in a predetermined order, and
the second error is next in sequence based on the predetermined order from the first error.

13. The method of claim 1, further comprising:
receiving a mode-selection input for cycling between or among two or more pulse-generator modes, wherein the pulse-generator modes comprise an IPG mode and an EPG mode; and
selecting a respective pulse-generator mode associated with the received mode-selection input.

14. The method of claim 1, further comprising:
receiving a user input requesting an error simulation; and
in response to receiving the user input, transmitting an instruction to the NP to display a simulation of the first error.

15. The method of claim 14, further comprising:
turning on an error indicator associated with the trainer device that indicates that an error is being simulated;
evaluating the response-information to determine if the corresponding user input resolves the first error; and
in response to determining that the corresponding user input resolves the first error, turning off the error indicator.

16. The method of claim 14, further comprising:
turning on an error indicator associated with the trainer device that indicates that an error is being simulated;
receiving error-resolution information from the NP indicating that the first error has been resolved; and
in response to receiving the error-resolution information, turning off the error indicator.

17. The method of claim 1, further comprising:
turning on one or more indicators on an interface of the trainer device, wherein the one or more indicators comprise:
a stimulation indicator that indicates whether or not the NP has successfully sent a command to the trainer device to turn on patient stimulation;
one or more pulse-generator mode indicators that indicate whether the simulation is simulating an IPG or an EPG; or
one or more error indicators that indicate whether an error is being simulated.

18. The method of claim 1, wherein the circuitry comprises:
a first circuitry for simulating the one or more neurostimulators; and
a second circuitry for simulating placement of a lead, wherein the second circuitry comprises a fixed load.

19. The method of claim 18, wherein the trainer device comprises a foramen needle stimulation cable and a ground electrode cable, wherein the foramen needle stimulation cable is configured to be connected to a first port of the NP, and wherein the ground electrode cable is configured to be connected to a second port of the NP, the method further comprising:
receiving, at the second circuitry, one or more electrical pulses from the NP, wherein the one or more electrical pulses form a completed circuit comprising the foramen needle stimulation cable, the ground electrode cable, and the fixed load of the second circuitry;
measuring an impedance of the completed circuit, wherein the impedance is associated with at least the fixed load; and
transmitting, to the NP, information corresponding to the measured impedance.

20. The method of claim 19, wherein the first circuitry and the second circuitry are housed on separate circuit boards that are not electrically coupled to each other.

21. The method of claim 18, wherein the trainer device comprises a lead stimulation cable and a ground electrode cable, wherein the lead stimulation cable is configured to be connected to a first port of the NP, and wherein the ground electrode cable is configured to be connected to a second port of the NP, the method further comprising:
receiving, at the second circuitry, one or more electrical pulses from the NP, wherein the one or more electrical pulses form a completed circuit comprising the lead stimulation cable, the ground electrode cable, and the fixed load of the second circuitry;
measuring an impedance of the completed circuit, wherein the impedance is associated with at least the fixed load; and
transmitting, to the NP, information corresponding to the measured impedance.

22. The method of claim 21, wherein the first circuitry and the second circuitry are housed on separate circuit boards that are not electrically coupled to each other.

23. The method of claim 1, wherein one or more retention pins of the trainer device is configured to be secured to one or more open ports of the NP.

24. The method of claim 1, wherein the trainer device is coupled to the NP wirelessly.

25. The method of claim 1, further comprising registering within a local memory of the trainer device that the first error has been resolved.

26. A trainer device for providing a simulation of a neurostimulator programming session, the trainer device comprising:
a portable housing;
circuitry disposed within the portable housing, wherein the circuitry is configured to:
couple the trainer device to a neurostimulator programmer (NP), wherein the NP is configured to program or adjust parameters of one or more neurostimulators, and wherein the trainer device is configured to simulate the one or more neurostimulators;
transmit a simulated first error information to the NP, wherein the first error information comprises an indication of a first error selected from a plurality of errors; and
receive a response-information from the NP corresponding to a user input entered by a user to resolve the first error.

27. A neurostimulator training system comprising:
a neurostimulator programmer (NP) configured to program or adjust parameters of one or more neurostimulators; and
a trainer device comprising:
a portable housing;
circuitry disposed within the portable housing, wherein the circuitry is configured to:
couple the trainer device to a NP, wherein the trainer device is configured to simulate the one or more neurostimulators;

transmit a simulated first error information to the NP, wherein the first error information comprises an indication of a first error selected from a plurality of errors; and
receive a response-information from the NP corresponding to a user input entered by a user to resolve the first error.

* * * * *